(12) United States Patent
Noda et al.

(10) Patent No.: US 6,756,230 B2
(45) Date of Patent: Jun. 29, 2004

(54) QUANTITATIVE ANALYSIS

(75) Inventors: Yuichiro Noda, Kyoto (JP); Yoshiyuki Tanaka, Kyoto (JP); Konomu Hirao, Kyoto (JP)

(73) Assignee: Arkray, Inc., Kyoto (JP)

( * ) Notice: Subject to any disclaimer, the term of this patent is extended or adjusted under 35 U.S.C. 154(b) by 424 days.

(21) Appl. No.: 09/858,986

(22) Filed: May 16, 2001

(65) Prior Publication Data

US 2001/0055784 A1 Dec. 27, 2001

(30) Foreign Application Priority Data

May 18, 2000 (JP) ........................................ 2000-146498

(51) Int. Cl.⁷ .............................................. G01N 31/00
(52) U.S. Cl. ............................... 436/8; 436/71; 436/74; 436/79; 436/86; 436/88; 436/174; 436/178; 435/16; 435/17; 435/21; 435/22; 435/24
(58) Field of Search ................................ 436/8, 13, 16, 436/17, 71, 74, 79, 86, 88, 125, 164, 174, 175, 177, 178; 422/101; 435/15, 16, 17, 21, 22, 24

(56) References Cited

U.S. PATENT DOCUMENTS 3,728,226 A 4/1973 Louderback 5,474,903 A * 12/1995 Huland ........................ 435/7.23
2001/0005488 A1 * 6/2001 Hirao et al. .................. 422/58

FOREIGN PATENT DOCUMENTS

| EP | 0 423 784 | 4/1991 |
| JP | 10-104226 | 4/1998 |
| WO | 97/40376 | 10/1997 |

* cited by examiner

Primary Examiner—Maureen M. Wallenhorst
(74) Attorney, Agent, or Firm—Merchant & Gould P.C.

(57) ABSTRACT

Amounts of components in a specimen can be analyzed with excellent quantitativity. The analysis includes: measuring an amount of a component to be analyzed in a specimen; measuring an amount of a standard component present originally and homeostatically in the specimen other than the component to be analyzed; determining the amount of the specimen from the amount of the standard component thus measured and a known concentration of the standard component in the specimen; and determining a concentration of the component to be analyzed in the specimen from the amount of the specimen thus determined and the amount of the component to be analyzed thus measured. The quantitative analysis of the present invention allows a component to be analyzed to be measured with high quantitativity as shown in FIG. 1.

19 Claims, 30 Drawing Sheets

(A)

(B)

QUANTITATIVE ANALYSIS

BACKGROUND OF THE INVENTION

1. Field of the Invention

The present invention relates generally to a quantitative analysis for determining amounts of components present in an unknown amount of specimen.

2. Related Background Art

Conventionally, a patient has been required to visit a medical institution and to have his blood, urine, or the like collected and tested, for medical treatments or diagnoses of various diseases. Usually, the test results are not available before the next medical examination or many hours. Hence, there has been a problem that such a test requires a considerably time-and-energy consuming process for both the patient and medical institution.

In order to avoid such a problem, recently, a specimen-collecting card formed, for example, of a filter paper has been proposed. For instance, JP 10-104226 A discloses a blood collecting card. Such a card has been used in the following remote clinical diagnosis system. In this remote clinical diagnosis system, a patient collects blood by himself and the blood collecting card is impregnated with the blood. This is then dried and is then mailed to a medical institution. In the medical institution that has received this, a portion impregnated with the blood is cut out from the blood collecting card and the blood is extracted to be tested with respect to various test items. When the patient visits the medical institution, medical treatments or diagnoses are conducted based on the test results.

When using such a blood collecting card, for example, since the patient himself collects blood as described above, the amount of blood with which the blood collecting card is impregnated is unknown. Hence, it has been difficult to correctly determine the amounts of components in the blood. From this viewpoint, for instance, the following methods have been proposed. In one example of the methods, filter paper capable of retaining a certain amount of blood in a certain area is used. A portion of the filter paper that has been impregnated with blood and has the certain area is cut out and thus the certain amount of blood is secured. In another example of the methods, filter paper having a certain area for retaining a certain amount of blood is used. A saturation amount of blood to be retained is supplied to the filter paper and thus the certain amount of blood is secured.

However, the aforementioned filter papers have the following problems. For instance, when using the former filer paper, the filter paper cut out is required to have been impregnated with blood throughout, and thus selection of the portion to be cut out or a cutting operation is difficult. On the other hand, when the latter filter paper is to be impregnated with a saturation amount of blood to be retained, actually, it is necessary to supply a larger amount of blood than the saturation amount to allow the filter paper to be impregnated sufficiently with the blood. Hence, time and energy are required and thus a great burden is imposed on the patient. Furthermore, when quantitativity is intended to be improved, the manufacture of such quantitative filter papers themselves becomes very complicated and difficult, and the manufacturing cost of such filter papers increases accordingly.

Besides the methods using porous materials such as the above-mentioned filter papers, for instance, there is a method of retaining and preserving a specimen using a capillary tube with the specimen remaining in a liquid state. In this case, however, there is possibility that the specimen thus retained may be dried, or when the blood is recovered from the capillary tube using, for example, a buffer solution, the amount of the specimen contained in the recovered liquid may become unknown and thus the quantitative accuracy may be deteriorated with respect to the amounts of the components actually contained in the specimen.

SUMMARY OF THE INVENTION

The present invention at least in its preferred embodiments is intended to provide a quantitative analysis in which even when an unknown amount of specimen is used, amounts of components in the specimen can be measured with high accuracy.

In order to achieve the above-mentioned object, a quantitative analysis of the present invention is used for measuring a concentration of a component to be analyzed in a specimen. The quantitative analysis includes: measuring an amount of a component to be analyzed in a specimen; measuring an amount of a standard component present originally and homeostatically in the specimen other than the component to be analyzed; determining an amount of the specimen from the amount of the standard component thus measured and a known concentration of the standard component in the specimen; and determining a concentration of the component to be analyzed in the specimen from the amount of the specimen thus determined and the amount of the component to be analyzed thus measured. In the present invention, the standard component denotes a substance that is originally present in the specimen and has a concentration maintained to have homeostasis (to be substantially invariable), for example, in vivo.

As described above, in the quantitative analysis of the present invention, not only the amount of the component to be analyzed in the specimen but also the amount of the standard component are measured. Thus, the concentration of the component to be analyzed in the specimen can be determined with excellent accuracy. Accordingly, the quantitativity is improved with respect to the component to be analyzed in the specimen. The standard component is a substance contained homeostatically in the specimen as described above and thus the content thereof in the specimen is known. Hence, its theoretical value (concentration) can be predetermined. Thus, for example, even in the case of a test sample containing an unknown amount of specimen, the rate of content (for example, the dilution or concentration ratio) of a specimen in the test sample can be determined from the ratio between the known concentration of the standard component and the measured amount of the standard component. Then, the concentration of the component to be analyzed actually contained in the specimen can be determined from the rate of content thus determined and the measured value of the component to be analyzed. Furthermore, according to the quantitative analysis of the present invention, it is possible to measure the amount of the component to be analyzed in the specimen without using, for example, a special porous material like one described above in order to improve the quantitativity. Thus, it also is possible to achieve cost reduction. In addition, for example, when a xenobiotica such as a dye, etc. is added as the standard material to the specimen beforehand, a problem in solubility may be caused or there is a possibility that the xenobiotica may affect the detection of the component to be analyzed. However, according to the present invention, since the aforementioned standard component is a substance originally present in the specimen, the standard component does not affect the analysis and an operation for adding such a xenobiotica is not required. Hence, the quantitative operation is simple and convenient. Consequently, the quantitative analysis of the present invention is particularly useful for various tests in clinical medical treatments, for example.

In the quantitative analysis of the present invention, preferably the specimen is retained in a porous material and is then recovered from the porous material to be analyzed. According to the quantitative analysis of the present invention, even when one of various porous materials is impregnated with an unknown amount of specimen collected by a patient himself and this is then dried and is then mailed to a medical institution as described above, the quantitative analysis of components to be analyzed in the specimen recovered as described above can be carried out easily. Hence, it is possible to save the time and energy of both the patient and medical institution, and thus the quantitative analysis of the present invention is useful for various tests in clinical medical treatments, etc., particularly for the remote clinical diagnosis system. Furthermore, the quantitative analysis of the present invention is useful, for example, for analyzing an unknown amount of specimen as described above but is not limited thereto as long as a specimen is retained in the porous material. Besides, the quantitative analysis of the present invention also is useful in the case, for instance, where a specimen retained in a capillary tube is collected as described above.

In the quantitative analysis of the present invention, preferably, the specimen is retained in the porous material, is dried, and is then recovered.

Furthermore, it also is preferable that the porous material retaining the specimen be dipped in an extractant and the specimen be extracted from the porous material to be recovered. As described later, the amount of the extractant is not limited, but preferably, is 1 to 1000 times the porous material by volume. In addition, preferably, a ratio of the extractant to the porous material per volume is constant.

Preferably, the quantitative analysis of the present invention includes: measuring an amount of a component to be analyzed in a test sample containing an extractant and the specimen recovered from the porous material; measuring an amount of the standard component to be analyzed in the test sample; determining an amount of the specimen from the amount of the standard component thus measured and a known concentration of the standard component in the specimen; and determining a concentration of the component to be analyzed in the specimen from the amount of the specimen thus determined and the amount of the component to be analyzed in the test sample thus measured.

In the quantitative analysis of the present invention, preferably, the concentration of the component to be analyzed contained in the specimen is determined by a formula of:

$$A = Z \times (Y/X),$$

where A denotes the concentration of the component to be analyzed, Z a measured concentration value of the component to be analyzed in the test sample, X a measured concentration value of the standard component, and Y a known concentration value of the standard component in the specimen.

In the quantitative analysis of the present invention, the standard component is not limited as long as it is contained homeostatically in the specimen. Examples of the standard component include sodium ion ($Na^+$), chloride ion ($Cl^-$), potassium ion ($K^+$), magnesium ion ($Mg^{2+}$), calcium ion ($Ca^{2+}$), total protein (hereinafter referred to as "TP"), and albumin (hereinafter referred to as "Alb"). Among them, $Na^+$, $Cl^-$, $K^+$, $Mg^{2+}$, $Ca^{2+}$, and TP are preferable, $Na^+$, $Cl^-$, $Mg^{2+}$, $Ca^{2+}$, and TP are more preferable, and $Na^+$, $CL^-$, and TP are particularly preferable.

In the quantitative analysis of the present invention, preferably, the specimen is an aqueous liquid specimen derived from an organism. Examples of the specimen include blood, urine, saliva, lymph, a cerebrospinal fluid, and an intercellular fluid. Among them, a preferable specimen is blood or the intercellular fluid, and a more preferable specimen is blood. Any one of, for example, whole blood, blood cells, blood plasma, and blood serum can be used as the blood specimen. Preferably, the blood specimen is whole blood, blood plasma, or blood serum and more preferably, is blood plasma or blood serum. When the present invention is applied to the quantitation of such a specimen derived from an organism, for example, various diagnoses in clinical medical treatments can be conducted with high accuracy.

In the quantitative analysis of the present invention, the component to be analyzed is not limited. When the specimen is blood (blood plasma, blood serum, etc.), examples of the component to be analyzed include glutamic-oxaloacetic transaminase (GOT), glutamic-pyruvic transaminase (GPT), γ-glutamyl transpeptidase (γ-GTP), creatine kinase (CPK), triglyceride (TG), amylase (Amy), HDL-cholesterol (HDL-C), and alkaline phosphatase (ALP).

DETAILED DESCRIPTION OF THE INVENTION

Figure 1:
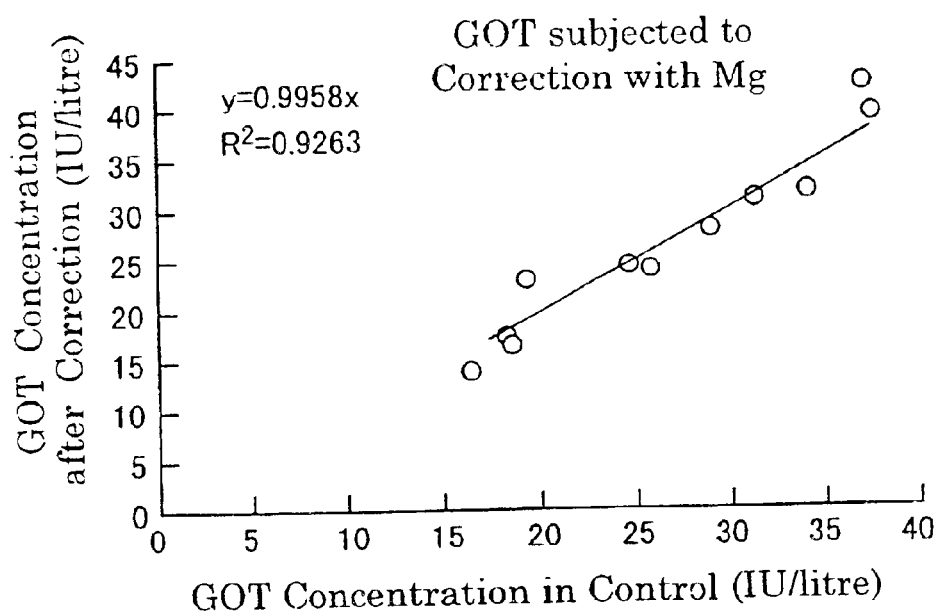
FIG. 1 is a graph showing the relationship between a GOT concentration obtained by correcting a GOT measured concentration with a Mg measured value and a GOT concentration in a control according to an example of the present invention.
Figure 2:
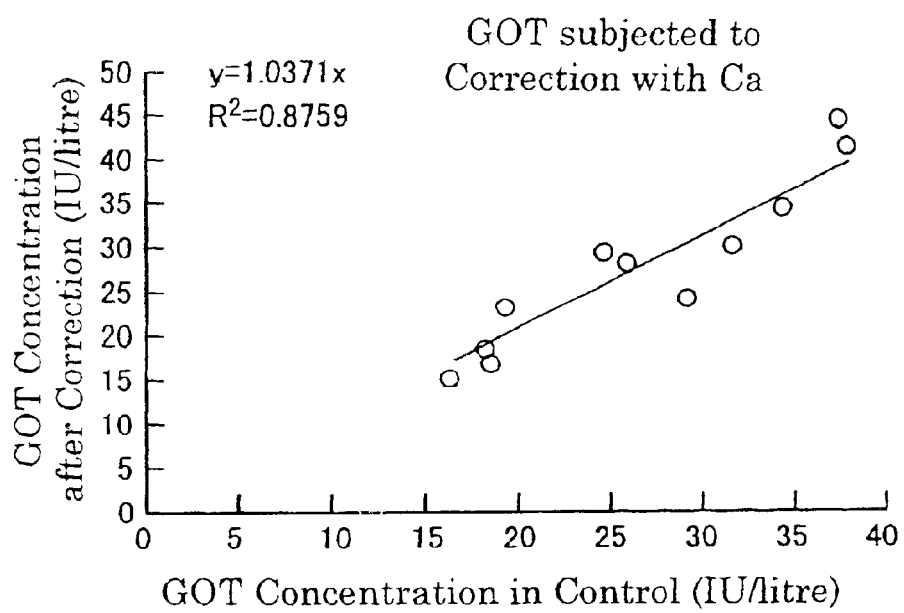
FIG. 2 is a graph showing the relationship between a GOT concentration obtained by correcting the GOT measured concentration with a Ca measured value and the GOT concentration in the control according to the example.
Figure 3:
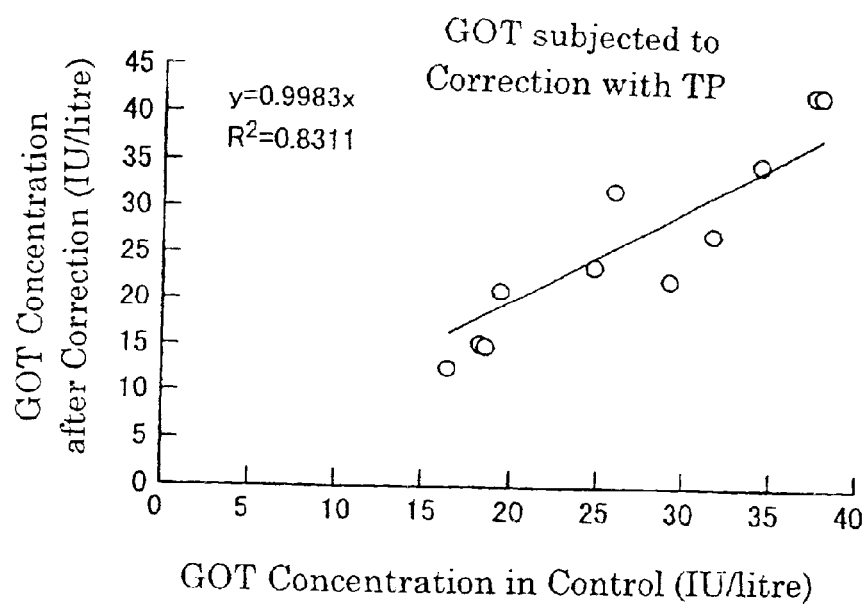
FIG. 3 is a graph showing the relationship between a GOT concentration obtained by correcting the GOT measured concentration with a TP measured value and the GOT concentration in the control according to the example.
Figure 4:
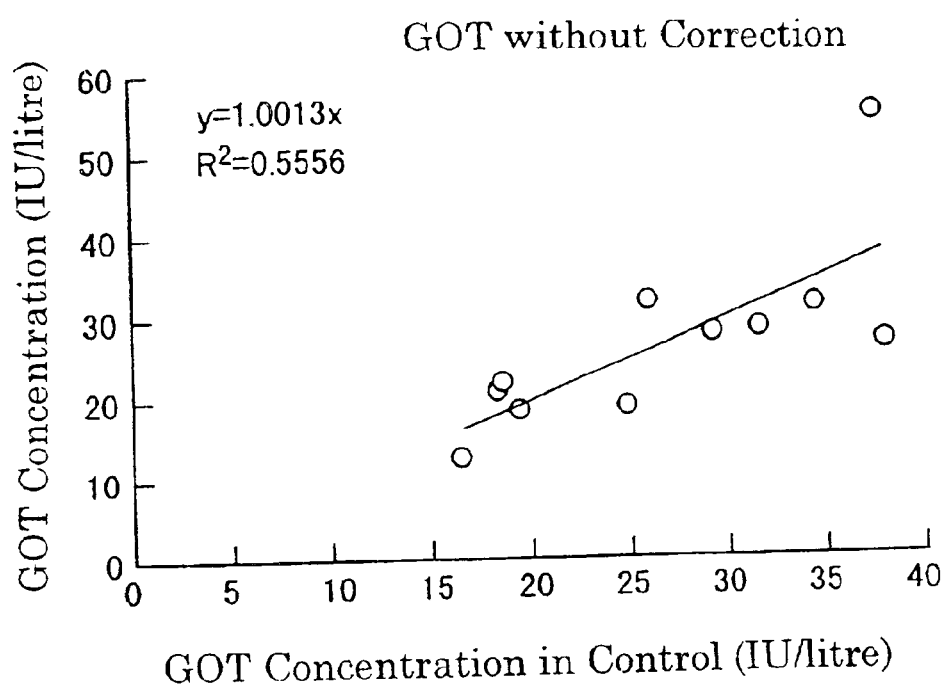
FIG. 4 is a graph showing the relationship between the GOT measured concentration and the GOT concentration in the control according to a comparative example.
Figure 5:
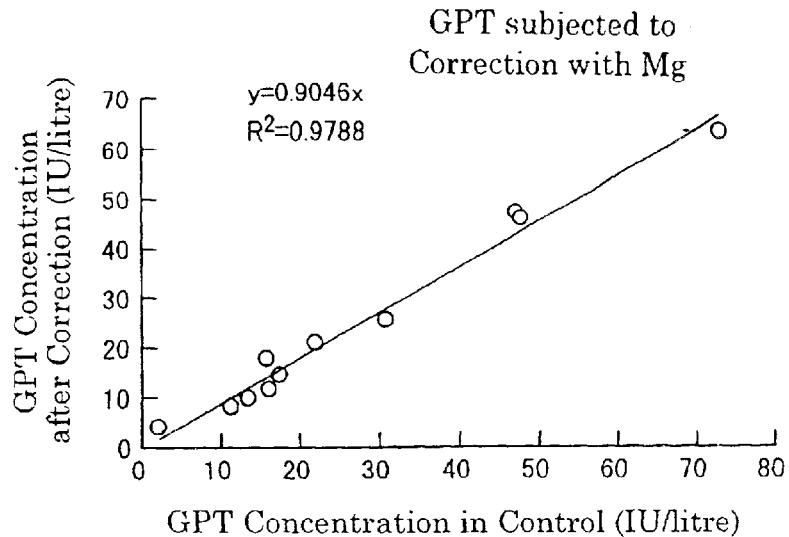
FIG. 5 is a graph showing the relationship between a GPT concentration obtained by correcting a GPT measured concentration with the Mg measured value and a GPT concentration in the control according to the example.
Figure 6:
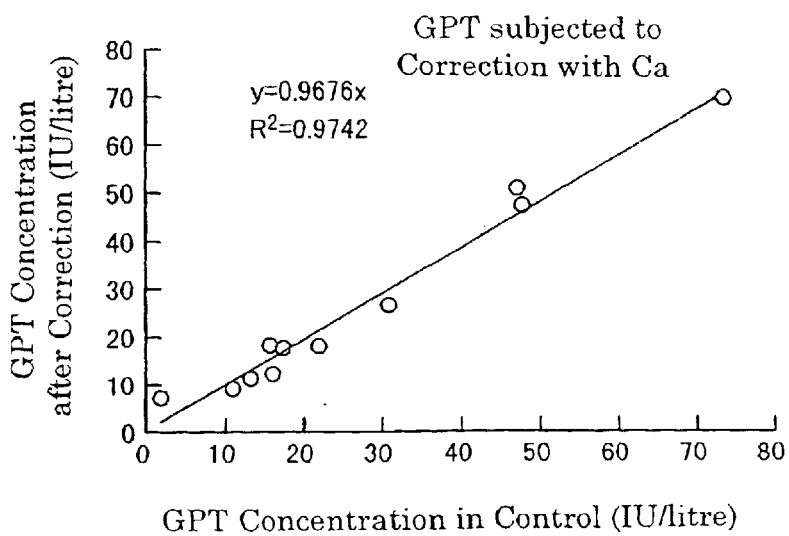
FIG. 6 is a graph showing the relationship between a GPT concentration obtained by correcting the GPT measured concentration with the Ca measured value and the GPT concentration in the control according to the example.
Figure 7:
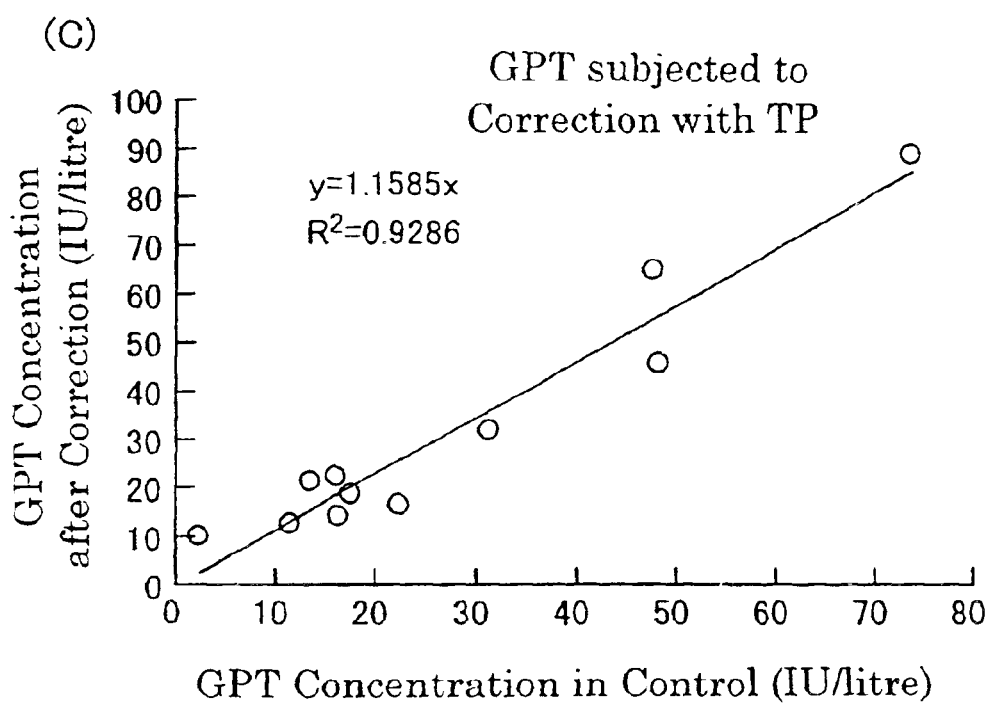
FIG. 7 is a graph showing the relationship between a GPT concentration obtained by correcting the GPT measured concentration with the TP measured value and the GPT concentration in the control according to the example.
Figure 8:
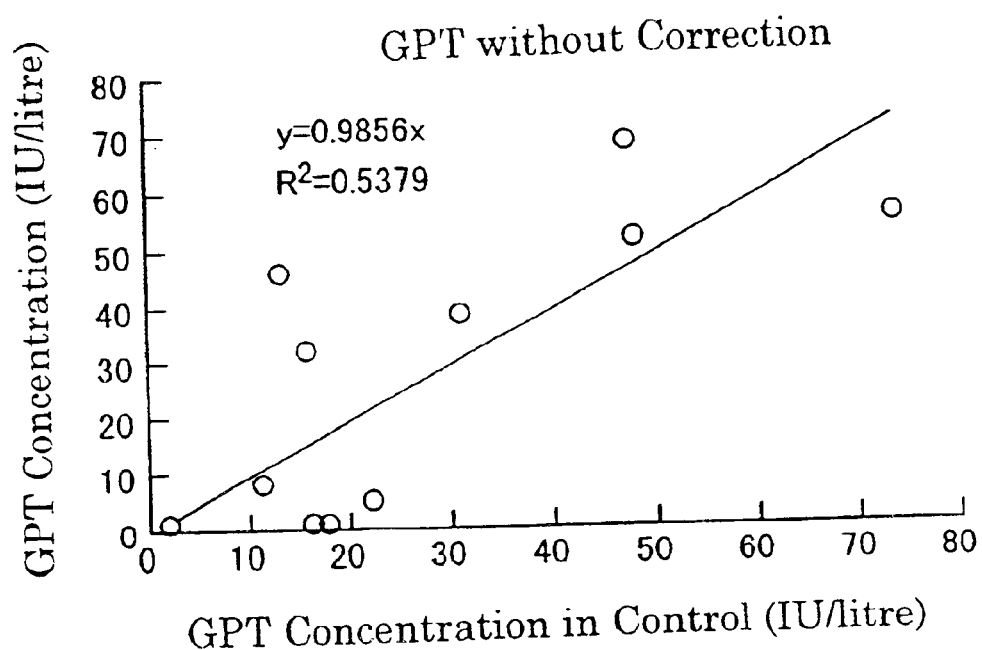
FIG. 8 is a graph showing the relationship between the GPT measured concentration and the GPT concentration in the control according to the comparative example.
Figure 9:
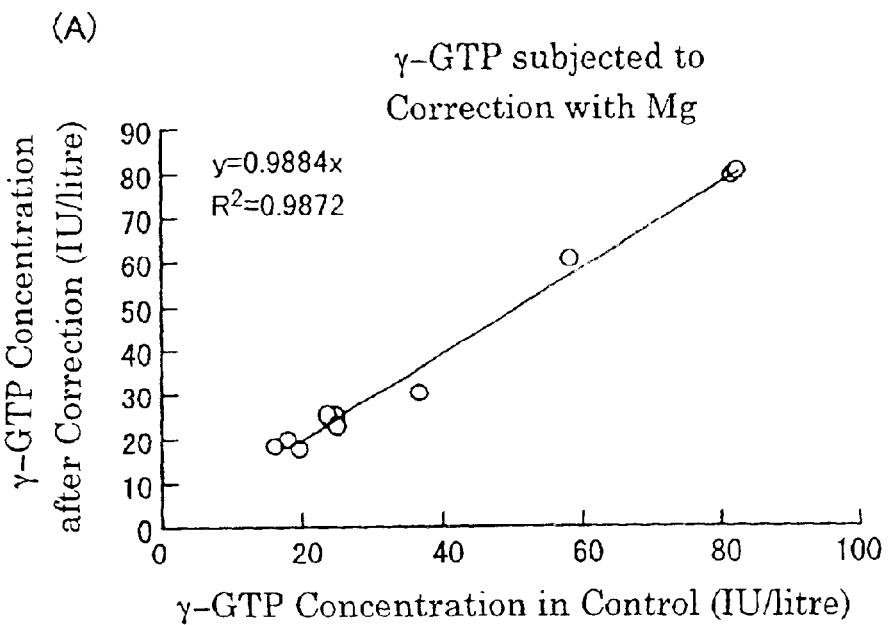
FIG. 9 is a graph showing the relationship between a γ-GTP concentration obtained by correcting a γ-GTP measured concentration with the Mg measured value and a γ-GTP concentration in the control according to the example.
Figure 10:
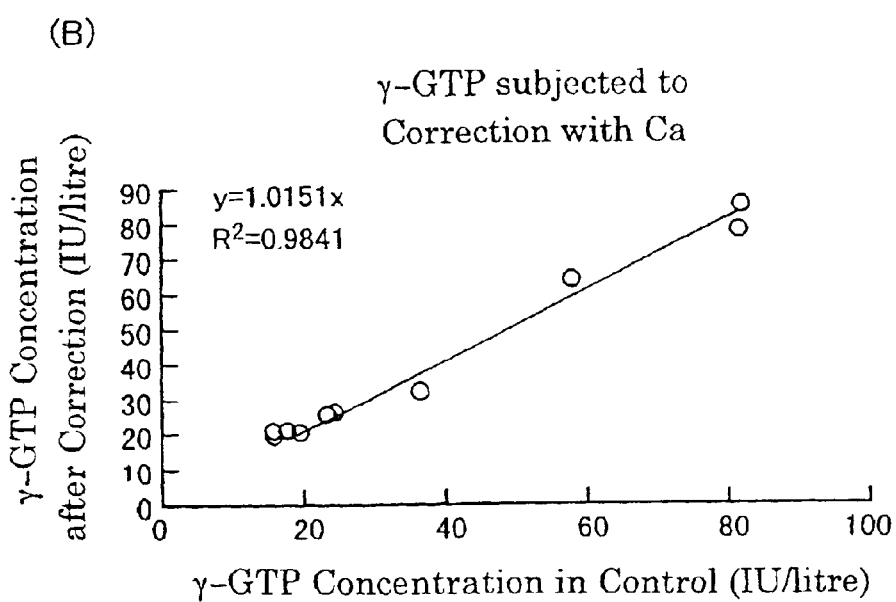
FIG. 10 is a graph showing the relationship between a γ-GTP concentration obtained by correcting the γ-GTP measured concentration by the Ca measured value and the γ-GTP concentration in the control according to the example.
Figure 11:
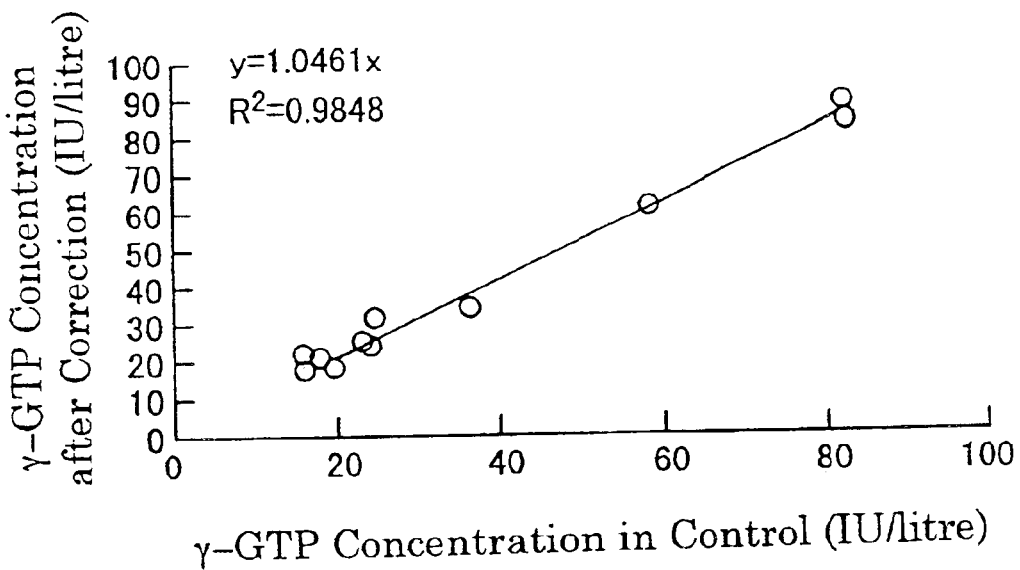
FIG. 11 is a graph showing the relationship between a γ-GTP concentration obtained by correcting the γ-GTP measured concentration with the TP measured value and the γ-GTP concentration in the control according to the example.
Figure 12:
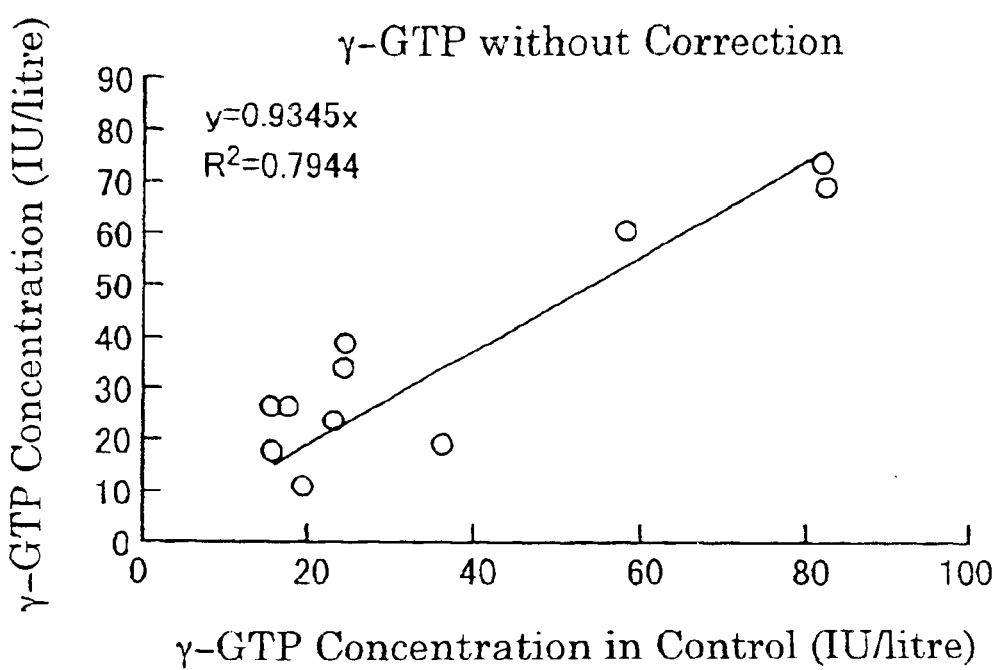
FIG. 12 is a graph showing the relationship between the γ-GTP measured concentration and the γ-GTP concentration in the control according to the comparative example.
Figure 13:
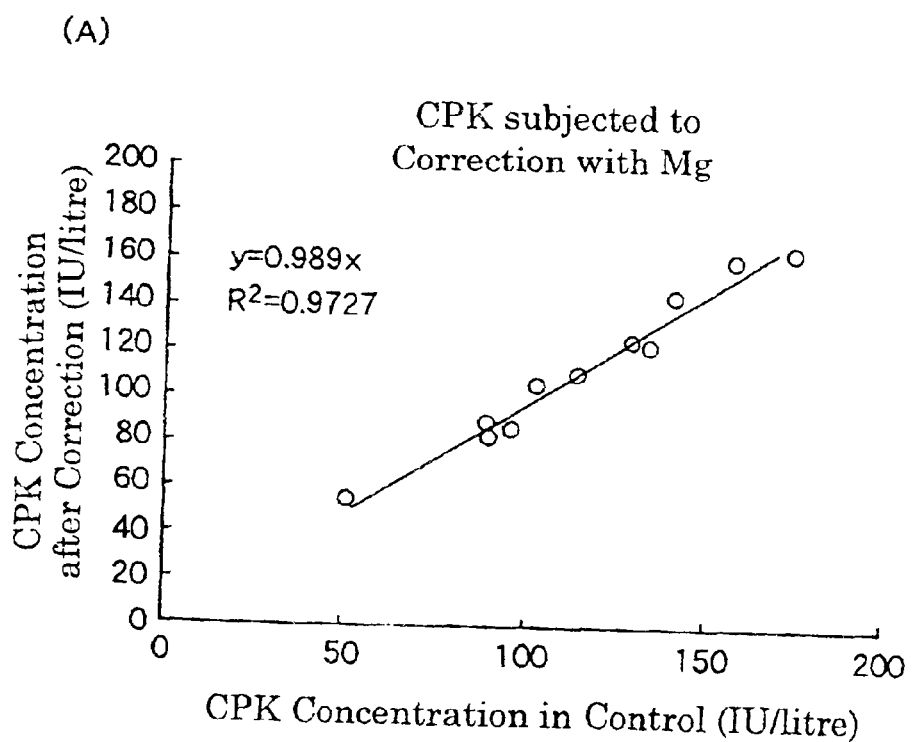
FIG. 13 is a graph showing the relationship between a CPK concentration obtained by correcting a CPK measured concentration with the Mg measured value and a CPK concentration in the control according to the example.
Figure 14:
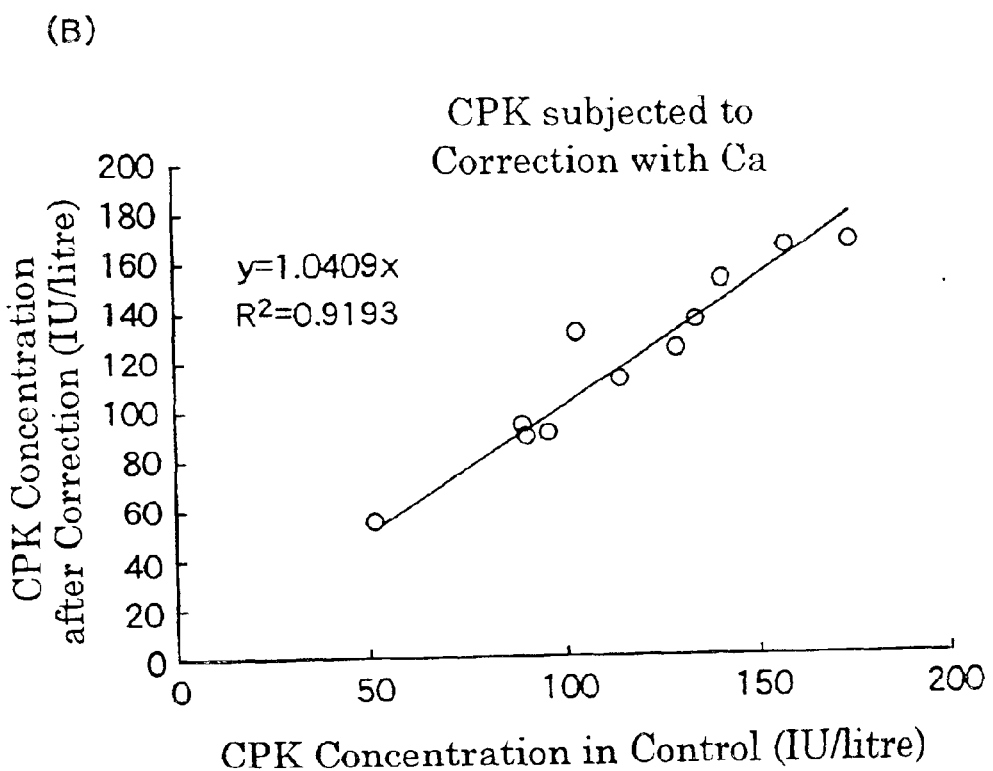
FIG. 14 is a graph showing the relationship between a CPK concentration obtained by correcting the CPK measured concentration with the Ca measured value and the CPK concentration in the control according to the example.
Figure 15:
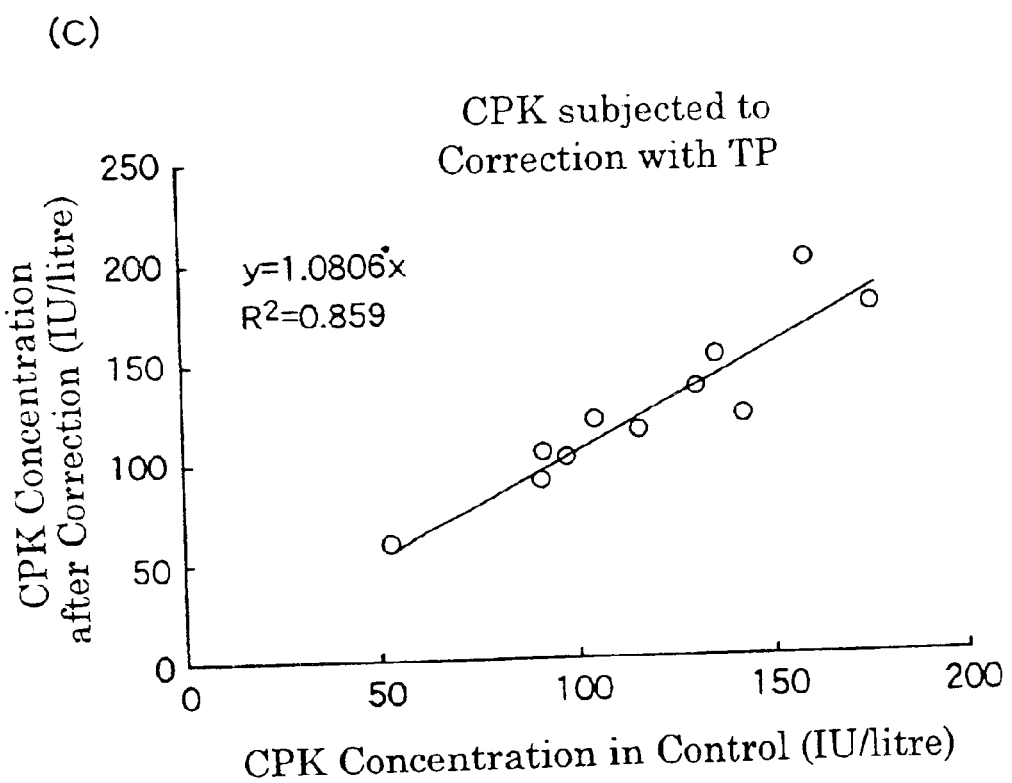
FIG. 15 is a graph showing the relationship between a CPK concentration obtained by correcting the CPK measured concentration with the TP measured value and the CPK concentration in the control according to the example.
Figure 16:
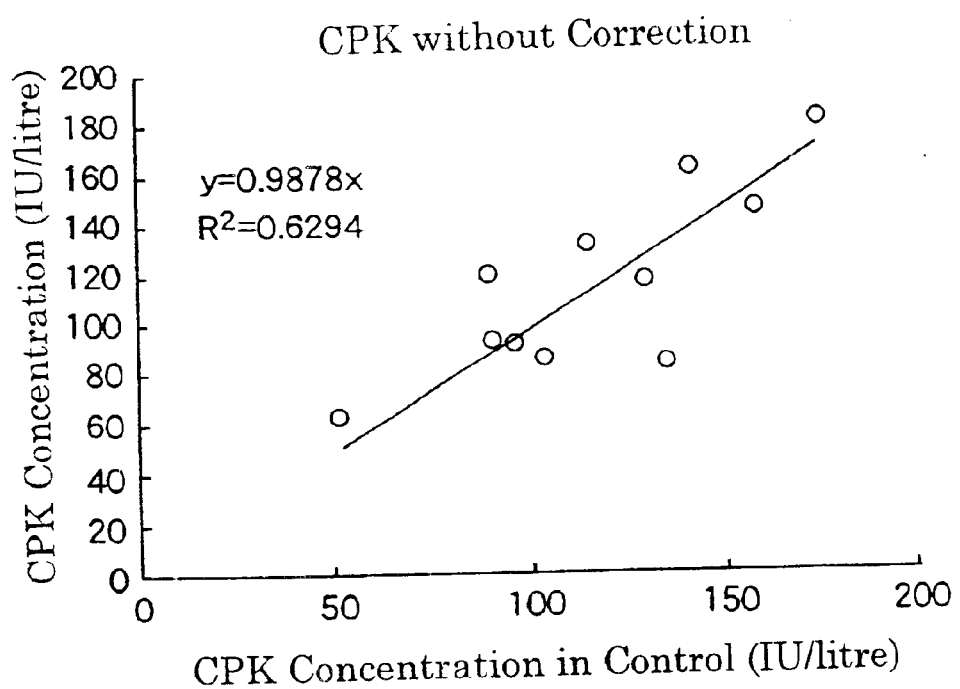
FIG. 16 is a graph showing the relationship between the CPK measured concentration and the CPK concentration in the control according to the comparative example.
Figure 17:
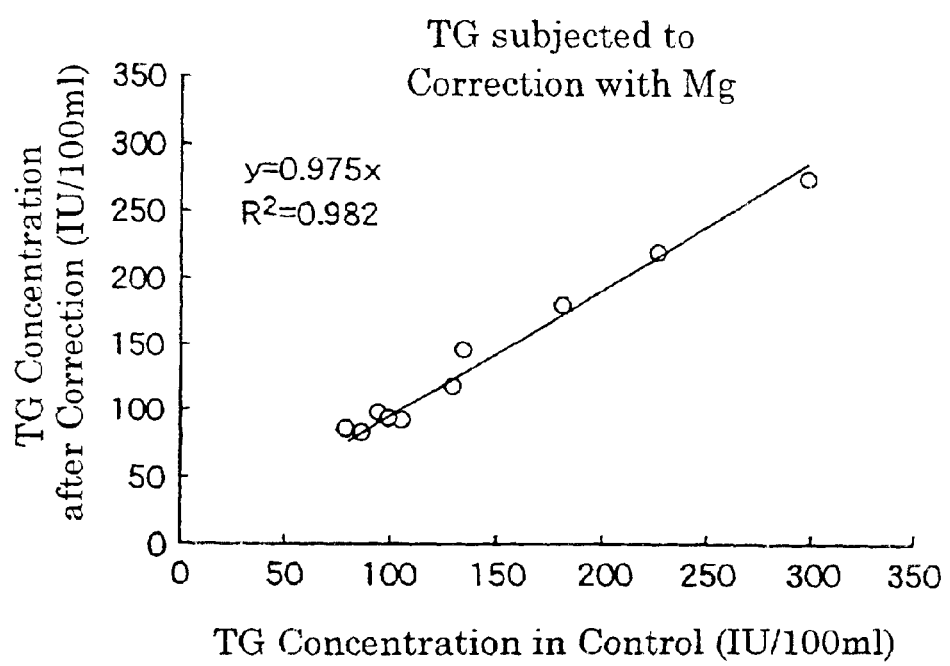
FIG. 17 is a graph showing the relationship between a TG concentration obtained by correcting a TG measured concentration with the Mg measured value and a TG concentration in the control according to the example.
Figure 18:
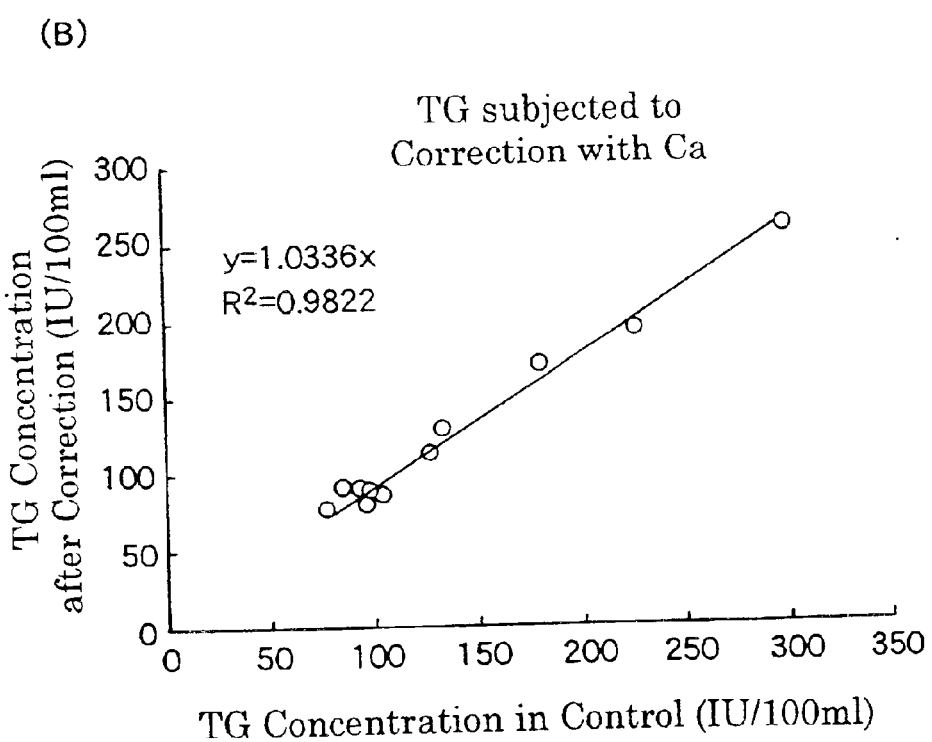
FIG. 18 is a graph showing the relationship between a TG concentration obtained by correcting the TG measured concentration with the Ca measured value and the TG concentration in the control according to the example.
Figure 19:
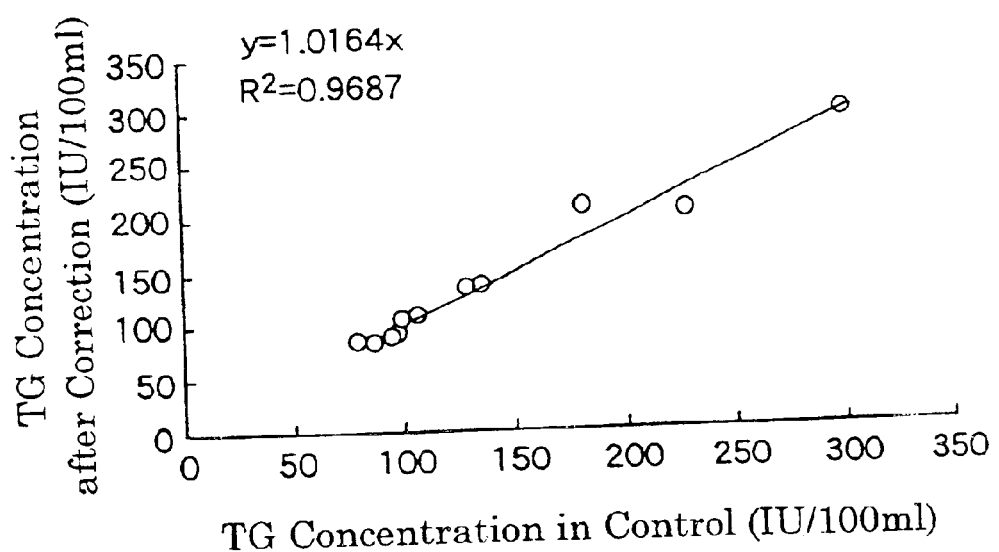
FIG. 19 is a graph showing the relationship between a TG concentration obtained by correcting the TG measured concentration with the TP measured value and the TG concentration in the control according to the example.
Figure 20:
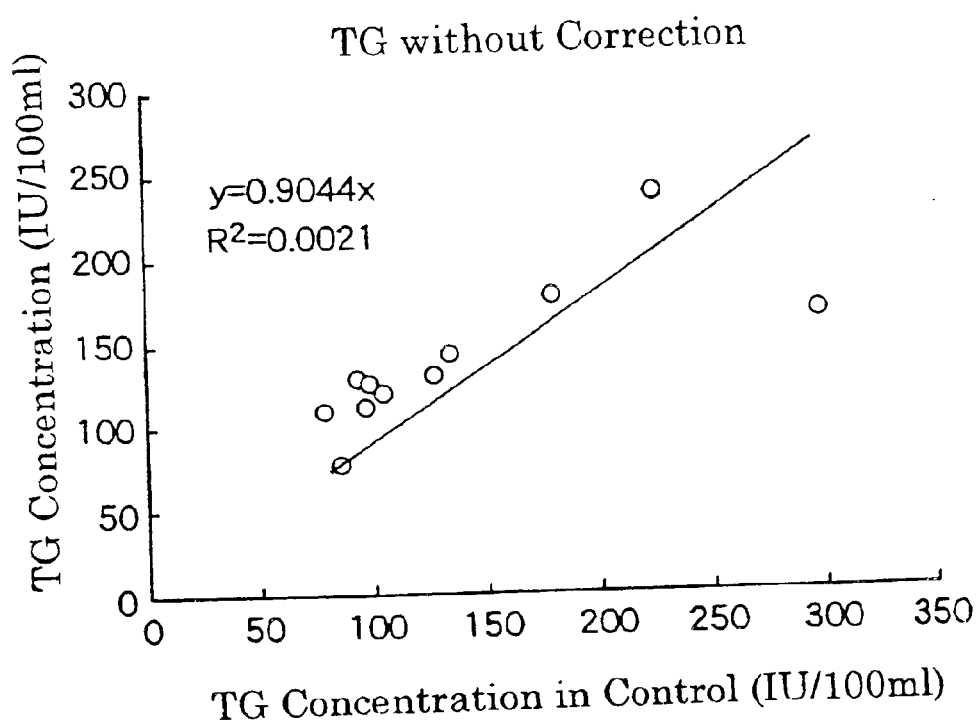
FIG. 20 is a graph showing the relationship between the TG measured concentration and the TG concentration in the control according to the comparative example.
Figure 21:
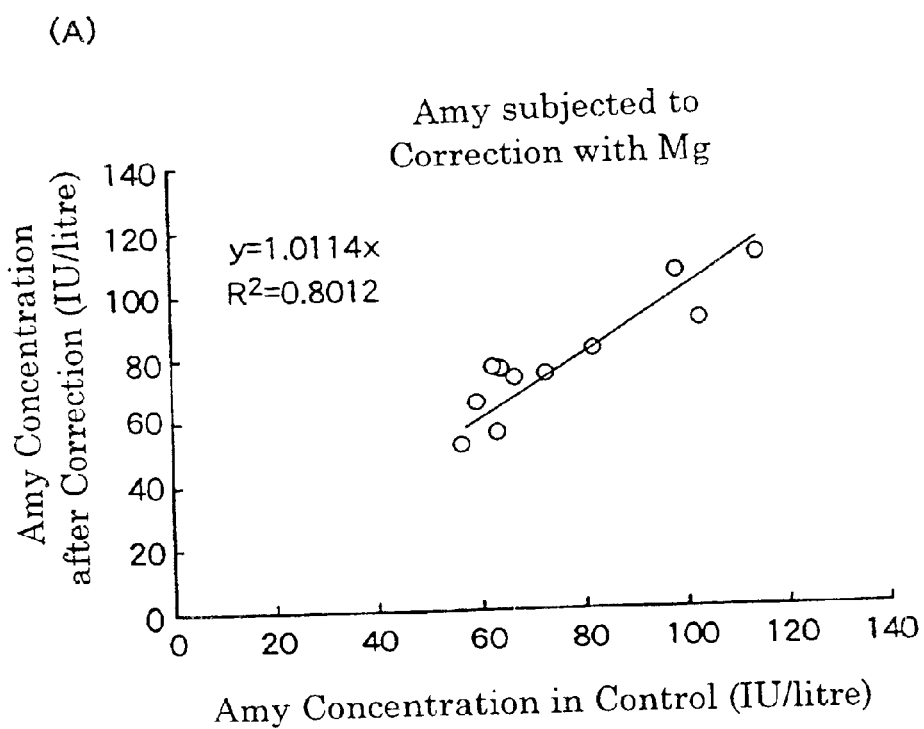
FIG. 21 is a graph showing the relationship between an Amy concentration obtained by correcting an Amy measured concentration with the Mg measured value and an Amy concentration in the control according to the example.
Figure 22:
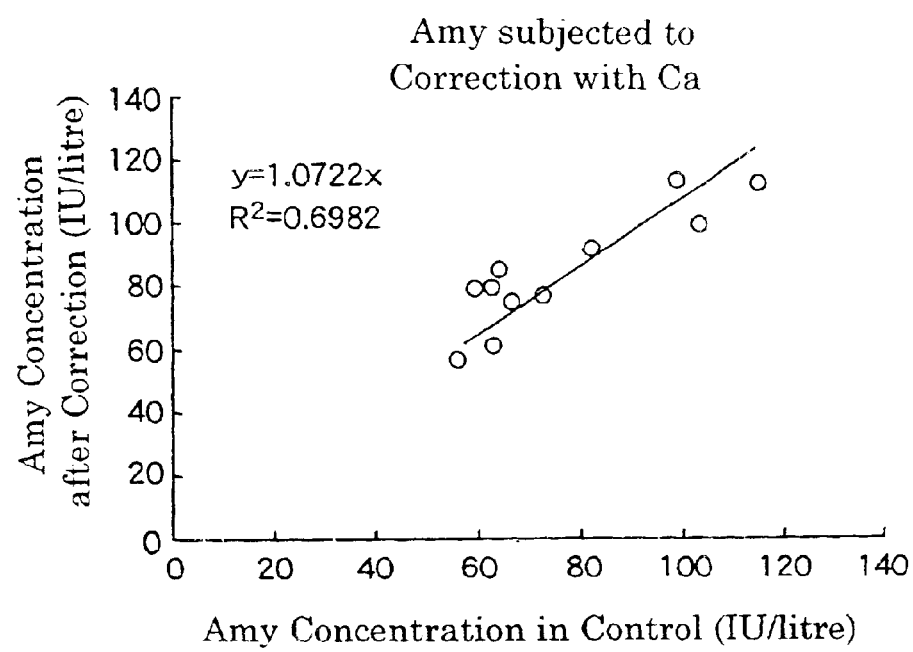
FIG. 22 is a graph showing the relationship between an Amy concentration obtained by correcting the Amy measured concentration with the Ca measured value and the Amy concentration in the control according to the example.
Figure 23:
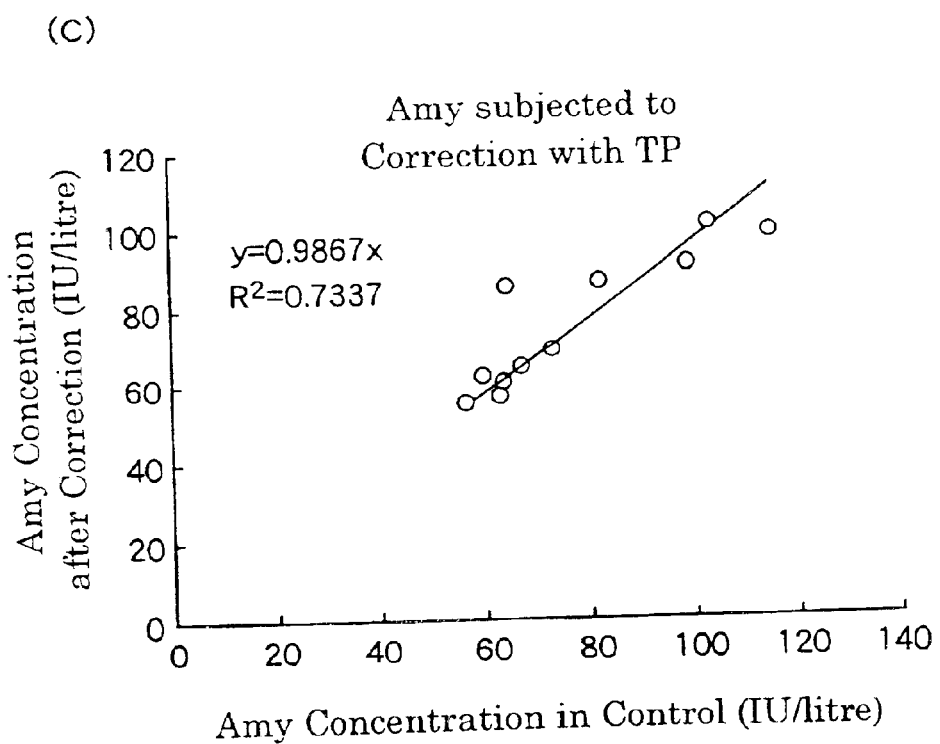
FIG. 23 is a graph showing the relationship between an Amy concentration obtained by correcting the Amy measured concentration with the TP measured value and the Amy concentration in the control according to the example.
Figure 24:
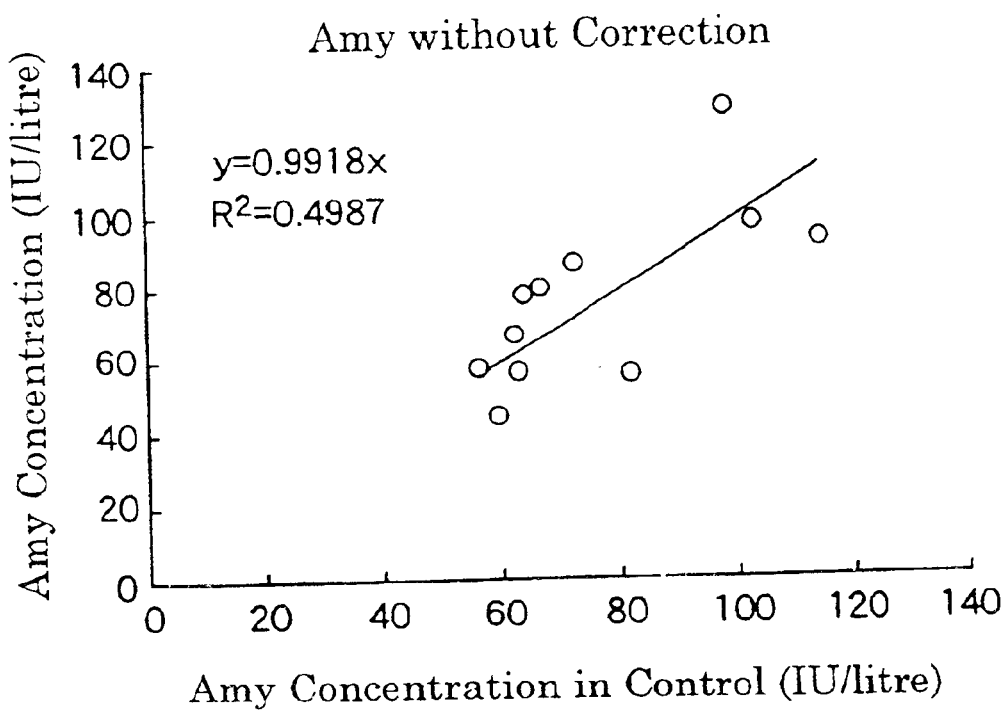
FIG. 24 is a graph showing the relationship between the Amy measured concentration and the Amy concentration in the control according to the comparative example.
Figure 25:
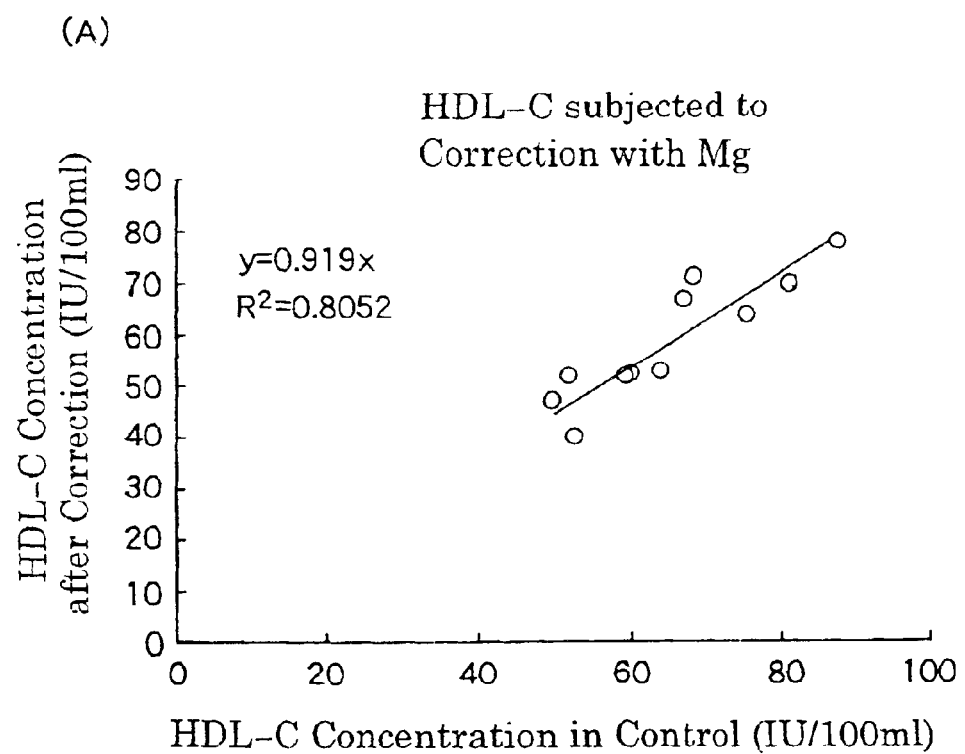
FIG. 25 is a graph showing the relationship between a HDL-C concentration obtained by correcting a HDL-C measured concentration with the Mg measured value and a HDL-C concentration in the control according to the example.
Figure 26:
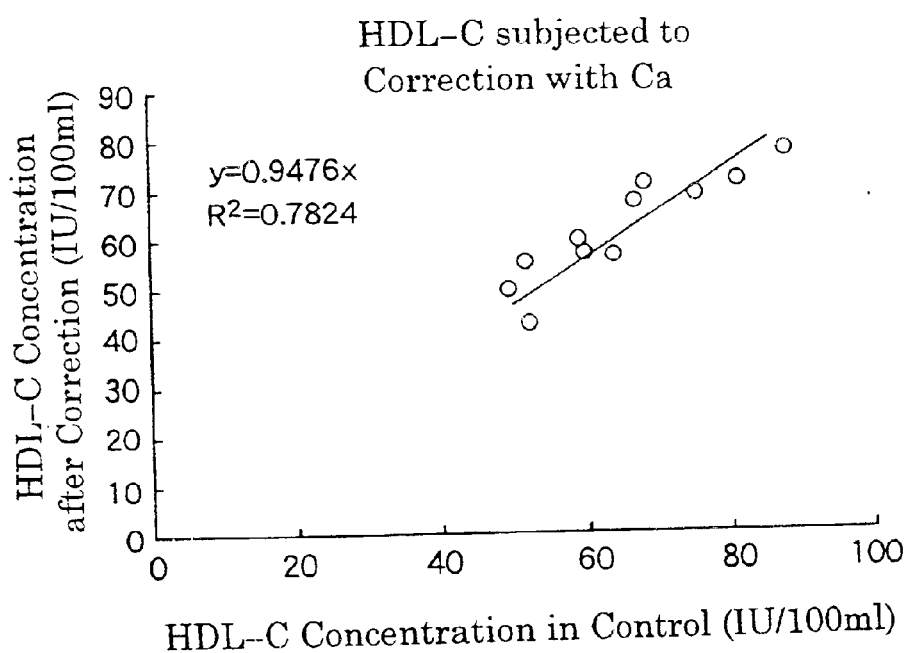
FIG. 26 is a graph showing the relationship between a HDL-C concentration obtained by correcting the HDL-C measured concentration with the Ca measured value and the HDL-C concentration in the control according to the example.
Figure 27:
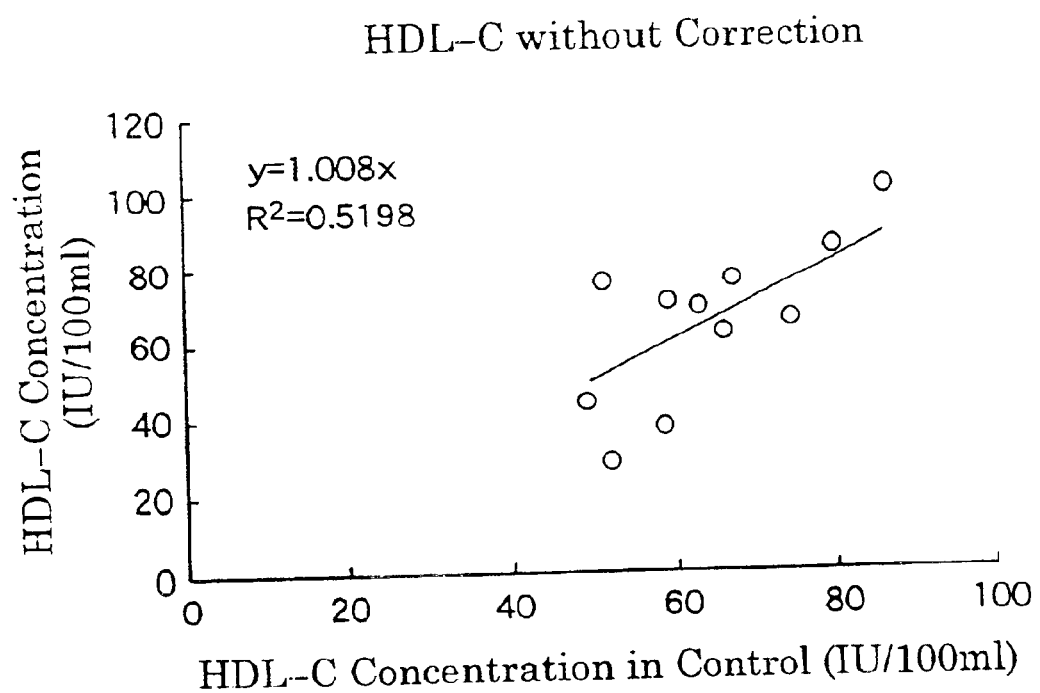
FIG. 27 is a graph showing the relationship between the HDL-C measured concentration and the HDL-C concentration in the control according to the comparative example.
Figure 28:
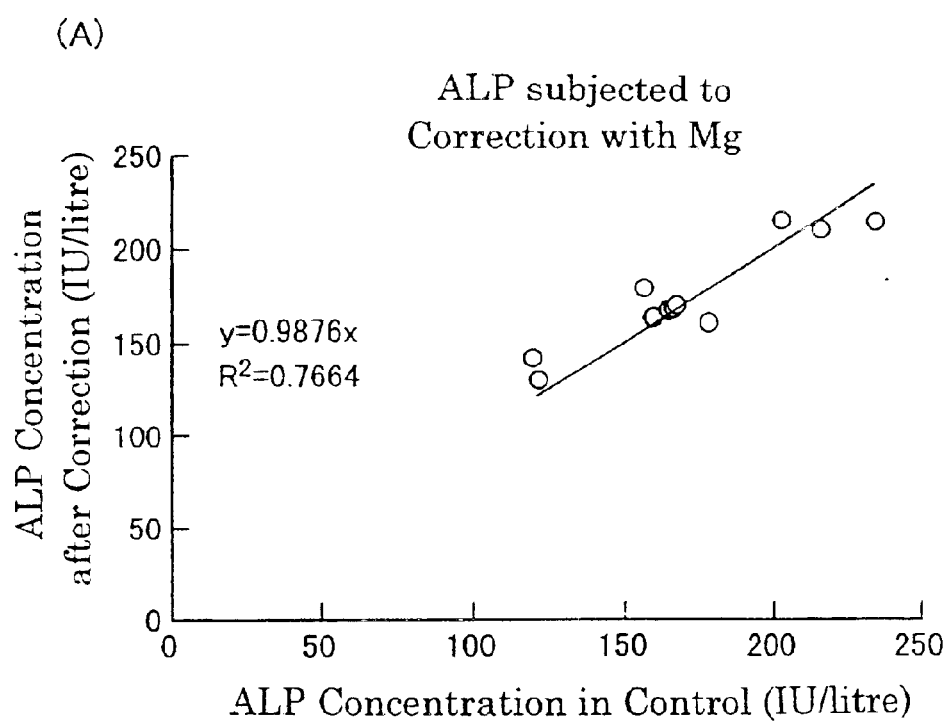
FIG. 28 is a graph showing the relationship between an ALP concentration obtained by correcting an ALP measured concentration with the Mg measured value and an ALP concentration in the control according to the example.
Figure 29:
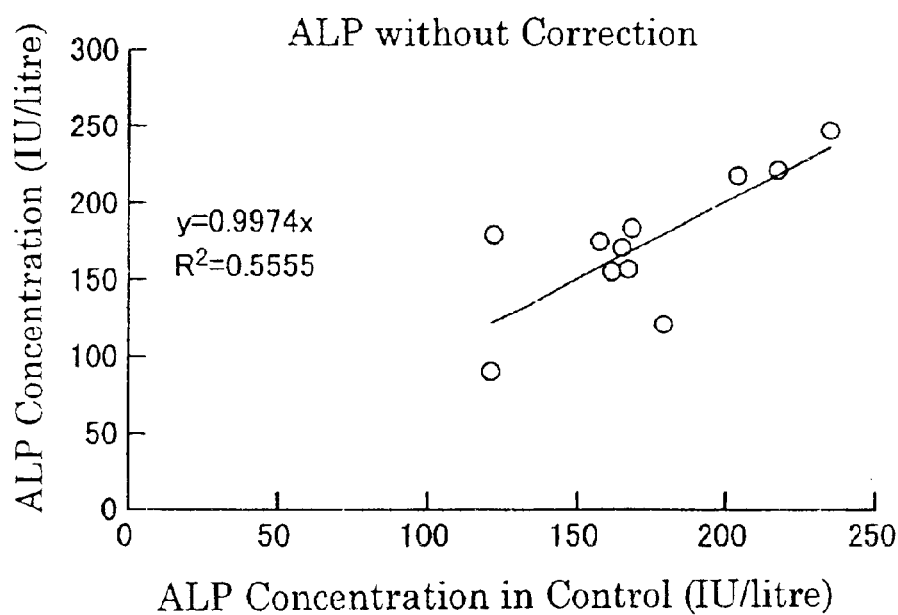
FIG. 29 is a graph showing the relationship between the ALP measured concentration and the ALP concentration in the control according to the comparative example.

The following description is directed to an example of a quantitative analysis according to the present invention.

Initially, a specimen is dropped on a porous material so that the porous material is impregnated with the specimen (or retains the specimen). This was dried by, for example, forced air drying or natural air drying, and then a specimen-impregnated portion of the porous material is cut out or punched out. For example, a punch can be used for the punching out. It is preferable that the place to be punched out retain many specimen-impregnated portions. According to the quantitative analysis of the present invention, however, since the amounts of components to be analyzed in an unknown amount of specimen can be determined, the quantitativity is not affected by the place to be punched out or by its area. For instance, unlike the cases of using such quantitative filter papers as described above, no problem is caused in quantitativity even when the place to be punched out includes portions that are not impregnated with the specimen.

A section obtained by the punching out or the like, for example, is cut into minute pieces and they are then put into a tube or the like. An extractant is added thereto and this is then left standing. Thus, the specimen is extracted. Subsequently, supernatant is recovered by, for example, centrifugation. The extractant is not limited as long as it can extract the specimen and does not affect the detection of the components to be analyzed in the specimen. For example, a buffer solution, a physiological salt solution, or purified water can be used as the extractant. In addition, a protein solution such as an albumin solution can be used as the extractant when it does not affect the measurement of the amounts of the components to be analyzed and standard components. Examples of the buffer solution include various buffer solutions containing, for instance, phosphoric acid, citric acid, hydrochloric acid, or acetic acid. The pH value of the buffer solution may be, for example, in the range of 3 to 9, preferably in the range of 5 to 9, and more preferably in the range of 6 to 8. It is preferable that, for example, the amount of the extractant to be added be known and can be determined according to the size of the section or the like. Specifically, the amount of the extractant to be added may be, for example, in the range of 1 to 1000 times the volume of the section, preferably in the range of 1 to 100 times, more preferably in the range of 1 to 10 times. Preferably, for instance, the amount of the extractant to be added relative to the size of the section is set to be constant, because this allows the quantitativity further to be improved. The time for the extraction process is not limited, but may be, for example, in the range of 1 to 300 minutes, preferably in the range of 1 to 180 minutes, and more preferably in the range of 10 to 60 minutes.

Next, the recovered liquid is used as a test sample, and the amounts of the components to be analyzed and the standard components in the test sample are measured. Then, the amounts of the components to be analyzed in the specimen can be determined from the values thus obtained and known concentration values (invariable concentrations) of the standard components. Specifically, the amounts of the components to be analyzed can be determined as follows.

For instance, from a measured value (concentration X) of a standard component in the test sample and a known concentration value (concentration Y) of the standard component in the specimen, a dilution ratio (Y/X) of the specimen resulted from the extraction/recovery operation is determined. Then, a measured value (concentration Z) of a component to be analyzed in the test sample (in the recovered liquid) is multiplied by the dilution ratio (Y/X), so that the concentration [Z×(Y/X)] of the component to be analyzed actually contained in the specimen can be determined. In addition, when an amount (V) of the recovered liquid is measured, the amount of the specimen [V×(X/Y)] recovered from the porous material also can be determined from the liquid amount (V) and the dilution ratio (Y/X).

The standard component is not limited as long as it is a substance with a concentration maintained homeostatically, for example, in vivo as described above. Examples of the standard component include $Na^+$, $Cl^-$, $K^+$, $Mg^{2+}$, $Ca^{2+}$, and TP, as described above.

The concentrations of the standard components contained in the specimen are maintained homeostatically as described above and thus can be pre-known. When being blood serum or blood plasma, the specimen includes: $Na^+$ with a concentration of about 134 to 146 mEq/litre (with a mean value of about 140 mEq/litre); $Cl^-$ with a concentration of about 97 to 107 mEq/litre (with a mean value of about 102 mEq/litre); $K^+$ with a concentration of about 3.2 to 4.8 mEq/litre (with a mean value of about 4.0 mEq/litre); $Mg^{2+}$ with a concentration of about 1.5 to 2.0 mEq/litre (with a mean value of about 1.8 mEq/litre); $Ca^{2+}$ with a concentration of about 8.4 to 10.2 mEq/litre (with a mean value of about 9.3 mEq/litre); TP with a concentration of about 6.7 to 8.3 g/100 ml (with a mean value of about 7.5 g/100 ml), and Alb with a concentration of about 3.5 to 5.2 g/100 ml (with a mean value of about 4.3 g/100 ml).

The method of measuring the concentrations of the standard components is not limited. The concentrations of the standard components can be measured by conventionally known methods.

The concentrations of $Na^+$, $Cl^-$, and $K^+$ can be measured by, for example, flame photometry, a glass electrode method, a titration method, an ion selective electrode method, or a method of measuring enzyme activity of an enzyme whose activity varies depending on the different ion concentrations (concentrations of $Na^+$, $Cl^-$, and $K^+$) (an enzyme activity method). Among them, the ion selective electrode method is preferable. Using the ion selective electrode method, the concentrations can be measured, for example, as follows.

In the ion selective electrode method, for instance, a standard solution is dropped on one of two ion selective electrodes and blood serum on the other. After the passage of a certain time, the potential difference between the two electrodes is measured. When the ion concentrations in the standard solution are equal to those in the blood serum, the potential difference is zero. Based on this, calibration curves each of which indicates the relationship between a potential difference and ion concentration are prepared, and thus the ion concentrations in the blood serum are determined from the calibration curves and the potential differences actually measured. For the ion selective electrode method, for example, Spot Chem SE (product name, manufactured by Arkray, Inc.) can be used as measuring equipment.

The $Mg^{2+}$ concentration can be measured by, for example, the following xylidyl blue method. Xylidyl blue and $Mg^{2+}$ form a chelate through the reaction expressed by the following formula:

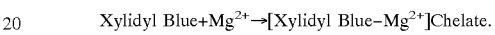

Xylidyl Blue+$Mg^{2+}$→[Xylidyl Blue–$Mg^{2+}$]Chelate.

The xylidyl blue absorbs light with a wavelength of 620 nm but the chelate does not. Therefore, the $Mg^{2+}$ concentration can be determined by measuring the decrease in absorbance with respect to this wavelength.

Specifically, for instance, a 3 μl sample is incubated at 37° C. and a 350 μl coloring reagent (containing 0.13 mmol/litre xylidyl blue I (xylylazoviolet I), 0.045 mmol/litre glycol ether diamine tetraacetic acid (GEDTA), and a surfactant) is added thereto. Thus, the reaction is started. The absorbance of the reacted solution after 7.5 minutes from the start of the reaction is measured with respect to a dominant wavelength of 660 nm and a sub wavelength of 700 nm. Then, the $Mg^{2+}$ concentration is determined from the measured values and a calibration curve prepared by the measurement of a Mg standard solution with a specific concentration.

Besides, the $Mg^{2+}$ concentration also can be measured by, for instance, the flame photometry, glass electrode method, titration method, ion selective electrode method, or enzyme activity method, as in the cases of measuring the $Na^+$ concentration, etc.

The $Ca^{2+}$ concentration can be measured by, for example, a methyl xylenol blue method as described below. The methyl xylenol blue and $Ca^{2+}$ form a chlate through the reaction expressed by the following formula:

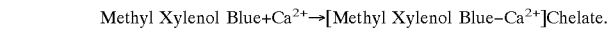

Methyl Xylenol Blue+$Ca^{2+}$→[Methyl Xylenol Blue–$Ca^{2+}$]Chelate.

The methyl xylenol blue does not absorb light with a wavelength of 600 nm but the chelate does. Therefore, the $Ca^{2+}$ concentration can be determined by measuring the increase in absorbance with respect to this wavelength.

Specifically, for instance, the $Ca^{2+}$ concentration can be measured as follows. A sample of 8 μl is mixed with 3.3 mol/litre monoethanolamine buffer solution (pH 12.0) of 400 μl, and this is then incubated at 37° C. After five minutes, a 200 μl coloring reagent (containing 0.29 mmol/litre methyl xylenol blue and 31 mmol/litre 8-quinolinol) is added thereto. Thus, the reaction is started. The absorbance of the reacted solution after five minutes from the start of the reaction is measured with respect to a dominant wavelength of 600 nm and a sub wavelength of 700 nm. Then, the $Ca^{2+}$ concentration is determined from the measured values and a calibration curve prepared by measuring the absorbance of a Ca standard solution with a specific concentration.

Besides, other methods also can be employed including, for instance, the flame photometry, glass electrode method, titration method, ion selective electrode method, or enzyme activity method, as in the cases of measuring the Na$^+$ concentration and the like.

The TP concentration can be measured by, for example, a Biuret method, Lowry method, Bradford method, copper chloride method, measuring method using a refractometer, etc. Among them, the Biuret method is preferable in view of its excellent convenience.

The Alb concentration can be measured by, for example, a method using a dye such as bromocresol green (hereinafter referred to as "BCG"). Alb and BCG are bonded to each other to form a blue green dye-bound substance. Therefore, the Alb concentration can be determined by measuring the absorbance of the blue green dye-bound substance.

Specifically, for example, a 3 μl sample is mixed with a 350 μl BCG reagent (containing 0.18 mM BCG, a 76 mM succinic acid buffer solution (pH 4.25), and a nonionic surfactant). This is then allowed to react together at 37° C. for 7.5 minutes. Then the absorbance of the reacted solution is measured with respect to wavelengths of 700 nm and 660 nm. Thus, the Alb concentration is determined from the measured values and a calibration curve prepared by measuring the absorbance of an Alb standard solution with a specific concentration.

As the porous material used for retaining the specimen as described above, for example, a filter paper, a glass filter, or a porous membrane made of resin can be used. Examples of the material of the porous membrane include polysulfone, polyester, nylon, cellulose nitrate, polycarbonate, and polyvinylidene fluoride. The porous membrane may be an asymmetric porous membrane having a pore structure with its average pore size varying gradually or continuously in the thickness direction or in a direction substantially parallel to a surface of the porous membrane (an anisotropic pore-size-gradient structure). One of such porous materials may be used individually or two types of such porous materials or more may be used together. The average pore size of the porous materials is not limited as long as it allows the specimen to penetrate and to be retained, but may be, for example, in the range of 0.1 to 1000 μm, preferably in the range of 0.1 to 100 μm, and more preferably in the range of 5 to 50 μm. The thickness of the porous material may be, for example, in the range of 10 to 1000 μm, preferably in the range of 100 to 500 μm, and more preferably in the range of 200 to 400 μm.

In order to stably maintain the components in the specimen to be retained, the porous material may contain a stabilizer such as, for example, saccharide such as sucrose, trehalose, lactose, glucose, etc., salt such as glycine, sodium chloride, potassium chloride, etc., or a buffer such as a phosphate buffer, a citrate buffer, a Good's buffer, etc. The content of the stabilizer can be determined according to its type or the like, but may be, for example, in the range of 0.01 to 10 mg per cubic centimeter of the porous material for retaining the specimen.

When the components to be analyzed are components in blood plasma or blood serum, it is preferable, for example, to stack a blood cell separation member on the porous material. This makes it unnecessary to carry out a blood cell separation operation as a pretreatment of a blood sample in the quantitative analysis of the present invention.

The material of the blood cell separation member is not limited. For instance, a glass filter or a porous resin membrane can be used as the material. The same materials as described above can be used as the material for the porous resin membrane. The average pore size of the porous membrane is not limited as long as it allows blood cells to be separated, but may be, for example, in the range of 0.1 to 100 μm. The porous membrane may be an asymmetric porous membrane having a pore structure, for example, with its average pore size varying continuously or gradually in the thickness direction in the porous membrane.

EXAMPLE

In this example, a serum specimen retained in a porous material was recovered, amounts of standard components and various components to be analyzed in the liquid thus recovered were measured, and thus the concentrations of the components to be analyzed in the serum specimen were determined. The specimen analyzing instrument, reagents, measuring method, etc. that were used in the example are described below.

Production of Specimen Analyzing Instrument

Figure 30:
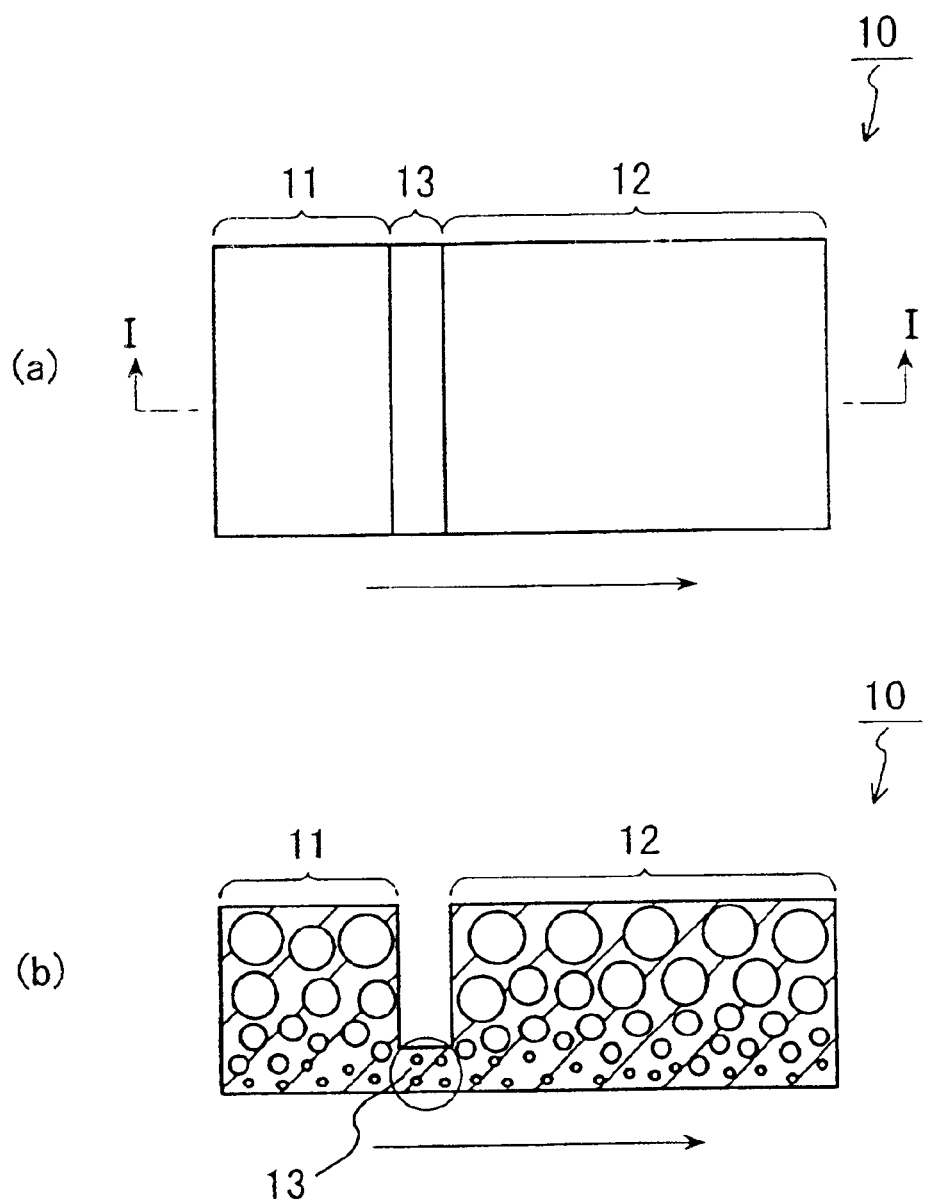
FIGS. 30A and 30B are a plan view and a sectional view, respectively, of a porous membrane of specimen analyzing instrument used in the example.

An asymmetric porous membrane (with a length of 35 mm, a width of 16 mm, a thickness of 320 μm, a maximum pore size of 100 μm, and a minimum pore size of 1 μm) with its average pore size varying in its thickness direction was dipped in a sucrose solution (with a concentration of 300 g/litre) and was then subjected to ultrasonication (50 kHz) for 15 minutes. This was then natural air dried. Afterward, an iron plate with a thickness of 1 mm was pressed against a portion at a location 11 mm along the length of the porous membrane with respect to one of its ends to form a groove in its width direction. Thus, the porous membrane shown in FIGS. 30A and 30B was prepared. FIG. 30A is a plan view showing the porous membrane thus processed. FIG. 30B is a sectional view taken in the direction I—I shown in the plan view. As shown in the figures, the porous membrane 10 processed as described above has a specimen supply section 11 and a specimen development section 12 that are separated by the groove formed in the width direction of the porous membrane 10. A blood cell separation section 13 is a portion between a bottom of the groove and a part of a surface of the asymmetric porous membrane corresponding to the bottom. In this porous membrane 10, the groove has a depth of 200 μm and a width of 1 mm, the specimen supply section 11 has a length of 11 mm, and the specimen development section 12 has a length of 23 mm. In the case of using this porous membrane 10, blood is dropped on a surface (the upper surface shown in FIG. 30B) of the specimen supply section 11 on the side with larger pores. While the blood moves in the thickness direction inside the specimen supply portion 11 and blood cells are separated, the blood moves in a direction (in the arrow direction shown in FIG. 30B) substantially parallel to the surface (hereinafter also referred to simply as a "surface direction"). Then, blood cells of the blood that has moved in the surface direction to reach the blood cell separation section 13 cannot pass through and are captured by the blood cell separation section 13. Consequently, only blood serum passes through the blood cell separation section 13 to be developed in the specimen development section 12.

Figure 31:
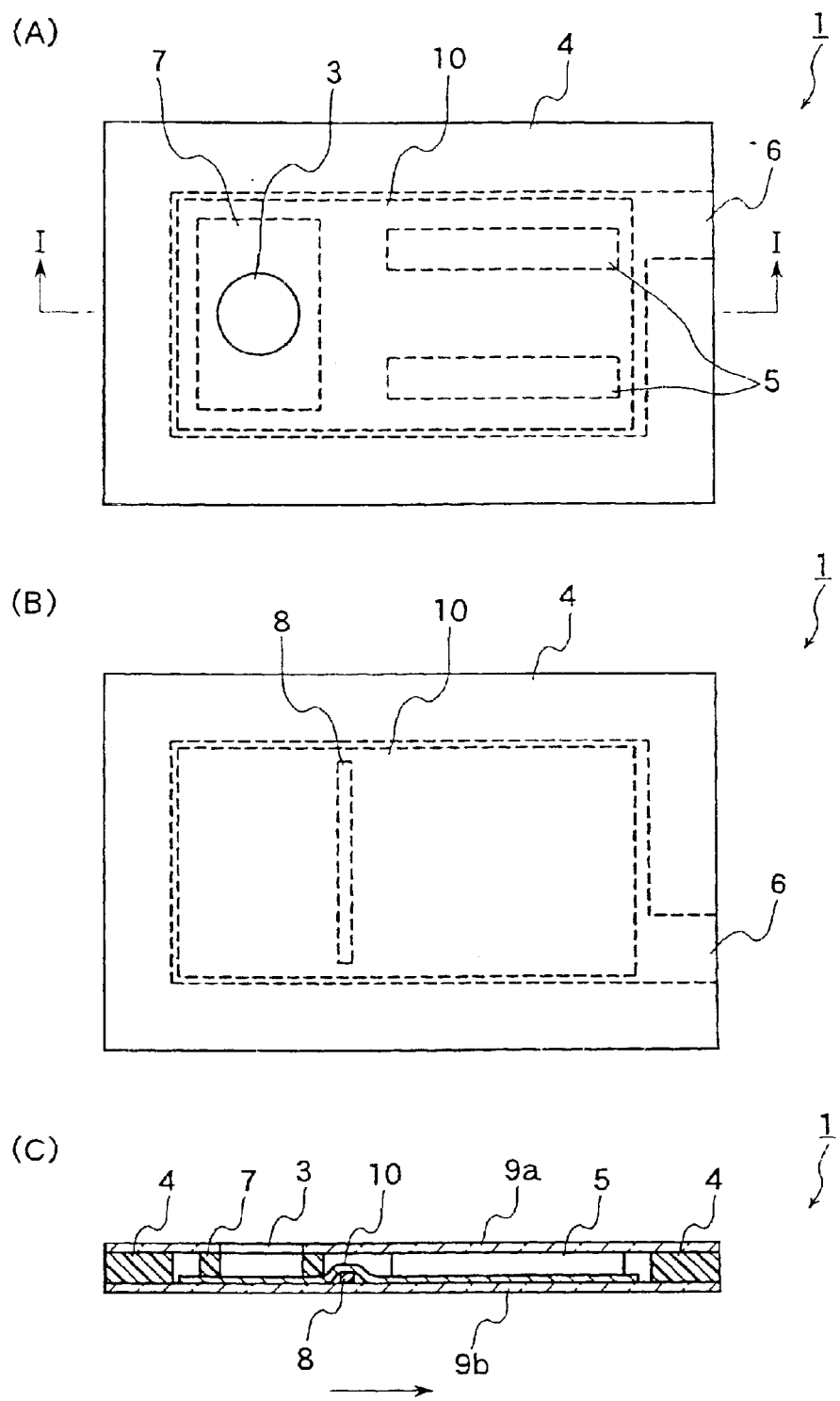
FIGS. 31A, 31B, and 31C are a plan view, a back side view, and a sectional view, respectively, of the specimen analyzing instrument.
Figure 32:
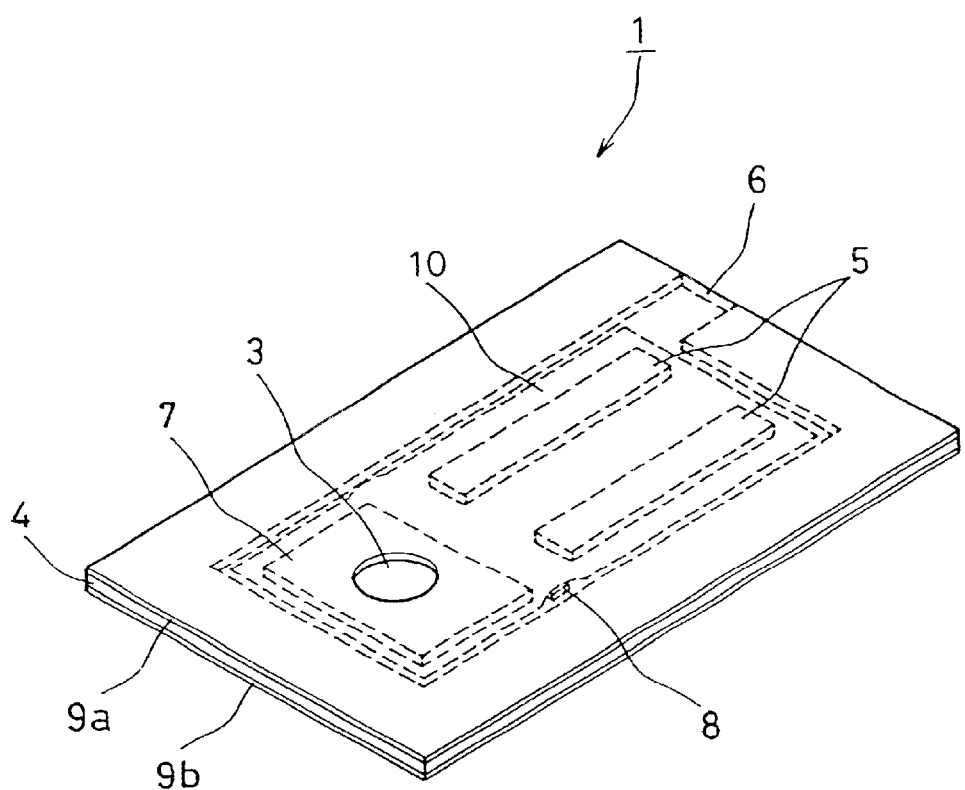
FIG. 32 is a perspective view of the specimen analyzing instrument.

This porous membrane 10 was set in a holder and thus the specimen analyzing instrument shown in FIGS. 31A, 31B, 31C and 32 was produced. FIG. 31A is a plan view showing this specimen analyzing instrument 1, FIG. 31B its back side view, and FIG. 31C a sectional view taken in the direction I—I shown in the plan view. FIG. 32 is its perspective view. In all the figures, the same portions are indicated with the same numerals and characters.

As shown in the figures, in this specimen analyzing instrument 1, a spacer 4 is placed around the periphery of a rectangular lower substrate 9b and a rectangular upper substrate 9a is placed thereon. Thus, the holder is formed and the porous membrane 10 is contained therein. A part of the periphery of the lower substrate 9b is not provided with the spacer 4 and thus a space between the upper substrate 9a and the lower substrate 9b is formed to serve as an air vent 6. On one side of the upper substrate 9a in its length direction, a hole 3 is formed for supplying a specimen, and the portion of the porous membrane 10 corresponding to the hole 3 is the center of the specimen supply section 11. On the inner face of the upper substrate 9a, a holding member 7 with a rectangular body is formed around the hole 3 and also has a hole communicating with the hole 3 accordingly, which serves as a specimen guide. On the inner face of the lower substrate 9b, a protruding supporter 8 is formed to protrude in the width direction at a location slightly closer to the center of the lower substrate 9b in the transverse direction than its portion corresponding to the hole 3 to the center. The protruding supporter 8 lifts a part of the blood cell separation section 13 of the porous membrane 10, whereby a gap is formed between the inner face of the lower substrate 9b and the porous membrane 10. Two holding members 5 with rectangular bodies formed on the inner face of the upper substrate 9a fix both ends of the development section 12 of the porous membrane 10 along its longitudinal direction to the inner wall of the lower substrate 9b.

Blood-Specimen Impregnation and Blood-Serum Recovery Methods

Through the hole 3 for specimen supply of the specimen analyzing instrument 1, about 100 µl whole blood of a healthy subject was dropped on the porous membrane 10. As described above, blood cells in the whole blood were separated in the blood-cell separation section 13 and blood serum was allowed to develop sufficiently in the development section 12. This was then natural-air-dried for 24 hours. Afterward, the porous membrane 10 was removed from the specimen analyzing instrument 1 and the development section 12 was cut out. The cut portion further was cut in a strip shape and thus cut pieces were obtained. The cut pieces were put into a test tube, to which a 150 µl PBS solution (phosphate-buffered saline, with pH 7.4, the same is true for the following description) was added as an extractant. This was left standing at room temperature for 20 minutes and was then subjected to centrifugation. As a result, supernatant was obtained and was used as a test sample. In the same manner as described above, a total of 11 test samples were prepared with whole blood of 11 healthy subjects, respectively. Then, as shown in the below, the respective test samples were subjected to the measurement of amounts of various standard components and various components to be analyzed. In this case, amounts of $Ca^{2+}$, $Mg^{2+}$, and TP as the standard components were measured.

The amounts of the respective standard components and various components to be analyzed were measured using the following commercially available measuring kits according to their application methods with an autoanalyzer (BM-8 manufactured by Nippon Electronic Co., Ltd.). In various measurements, purified water was used as a blank.

Measuring Kits for Standard Components
1. $Ca^{2+}$
Product Name: Calcium E-HA Test Wako (Wako Pure Chemical Industries, Ltd.) (a methyl xylenol blue method)
2. $Mg^{2+}$
Product Name: Magnesium—HRII (Wako Pure Chemical Industries, Ltd.) (a xylidyl blue method)
3. TP
Product Name: TP II-HA Wako (Wako Pure Chemical Industries, Ltd.)

Measuring Kits for Components to be Analyzed
1. Glutamic—Oxaloacetic Transaminase (GOT)
Product Name: Transaminase HR-II (GOT—7070: Wako Pure Chemical Industries, Ltd.)
2. Glutamic—Pyruvic Transaminase (GPT)
Product Name: Transaminase HR-II (GPT—7070: Wako Pure Chemical Industries, Ltd.)
3. γ-Glutamyl Transpeptidase (γ-GTP)
Product Name: γ-GTP J-HA Test Wako (Wako Pure Chemical Industries, Ltd.)
4. Creatine Kinase (CPK)
Product Name: CK E-HA Test Wako (Wako Pure Chemical Industries, Ltd.)
5. Triglyceride (TG)
Product Name: Triglyceride E-HA Test Wako (Wako Pure Chemical Industries, Ltd.)
6. Amylase (Amy)
Product Name: Amy II-HA Test Wako (Wako Pure Chemical Industries, Ltd.)
7. HDL-Cholesterol (HDL-C)
Product Name: Choletest HDL (Daiichi Pur Chemicals Co., Ltd.)
8. Alkaline Phosphatase (ALP)
Product Name: ALP II-HA Test Wako (7150: Wako Pure Chemical Industries, Ltd.)

As an example, measured values of the various components to be analyzed and various standard components in the test samples were substituted in the following formula (1) and thus the amounts of the various components to be analyzed in the blood serum specimens were determined.

Concentration of a component to be analyzed, contained in a specimen=$Z \times (Y/X)$ ... (1)

Z: Measured value (concentration) of a component to be analyzed in a test sample X: Measured value (concentration) of a standard component in the test sample Y: Known theoretical value (concentration) of the standard component in a specimen Known theoretical values (concentrations) of the standard components in the blood serum specimens are as follows: the $Mg^{2+}$ concentration is 1.8 mEq/litre, the $Ca^{2+}$ concentration 9.3 mEq/litre, and the TP concentration 7.5 g/100 ml. As a comparative example, the corrections with the standard components expressed by the formula (1) were not carried out. As a control, whole blood of the same healthy subjects was subjected to centrifugation, blood serum thus obtained was used, and amounts of various components to be analyzed in the blood serum were measured by the measuring method as described above.

With respect to the measurement results of the example, graphs were prepared, each of which shows a concentration of a component to be analyzed in the control (indicated in the x-axis) and a concentration of the component to be analyzed after a correction (indicated in the y-axis). Besides, with respect to the measurement results of the comparative example, graphs were prepared, each of which shows a concentration of a component to be analyzed in the control (indicated in the x-axis) and a concentration of the component to be analyzed subjected to no correction (indicated in the y-axis). Thus, correlation coefficients and slopes of the formulae expressing the respective relationships were determined. These results are shown in Tables 1 and 2 below.

TABLE 1

Correlation Coefficient $R^2$

| | Example | | | Comparative Example |
|---|---|---|---|---|
| | Correction with Mg | Correction with Ca | Correction with TP | |
| GOT | 0.926 | 0.876 | 0.831 | 0.556 |
| GPT | 0.979 | 0.974 | 0.929 | 0.538 |
| γ-GTP | 0.987 | 0.984 | 0.985 | 0.794 |
| CPK | 0.973 | 0.919 | 0.859 | 0.629 |
| TG | 0.982 | 0.982 | 0.969 | 0.0021 |
| Amy | 0.801 | 0.698 | 0.734 | 0.499 |
| HDL-C | 0.805 | 0.782 | — | 0.520 |
| ALP | 0.766 | — | — | 0.556 |

TABLE 2

Slopes in Correlation Equation

| | Example | | | Comparative Example |
|---|---|---|---|---|
| | Correction with Mg | Correction with Ca | Correction with TP | |
| GOT | 0.449 (0.996) | 0.467 (1.04) | 0.598 (0.998) | 0.119 (1.003) |
| GPT | 0.362 (0.905) | 0.395 (0.988) | 0.618 (1.16) | 0.0796 (0.986) |
| γ-GTP | 0.543 (0.988) | 0.558 (1.02) | 0.767 (1.05) | 0.114 (0.935) |
| CPK | 0.495 (0.989) | 0.521 (1.04) | 0.720 (1.08) | 0.125 (0.988) |
| TG | 0.584 (0.975) | 0.619 (1.03) | 0.813 (1.02) | 0.126 (0.904) |
| Amy | 0.606 (1.01) | 0.642 (1.07) | 0.789 (0.987) | 0.150 (0.992) |
| HDL-C | 0.460 (0.919) | 0.474 (0.948) | — | 0.106 (1.01) |
| ALP | 0.543 (0.988) | — | — | 0.114 (0.997) |

*The values indicated in the parentheses indicate slopes after multiplication by the coefficients.

FIGS. 1 to 29 show graphs obtained by plotting of concentration values obtained by multiplying the concentrations of the components to be analyzed after the corrections in the example and the concentrations of the components to be analyzed subjected to no correction in the comparative example, by the coefficients mentioned in Table 3 below. The coefficients serve to set the recovery of each component to be analyzed from the porous membrane to be 100%. These coefficients can be calculated from the recovery of the respective components to be analyzed and the respective standard components from the porous membrane. The recovery is determined as follows: for example, under the same conditions as described above, the porous membrane is impregnated with a known amount of blood serum specimen containing a component to be analyzed with a known concentration, then the blood serum specimen is recovered from the porous membrane, and the component to be analyzed and the standard component in the recovered liquid are measured.

TABLE 3

Coefficients for Various Components

| | Standard Component | | |
|---|---|---|---|
| Component to be analyzed | $Mg^{2+}$ | $Ca^{2+}$ | TP |
| GOT | 2.22 | 2.22 | 1.67 |
| GPT | 2.50 | 2.05 | 1.88 |
| γ-GTP | 1.82 | 1.82 | 1.36 |

TABLE 3-continued

Coefficients for Various Components

| | Standard Component | | |
|---|---|---|---|
| Component to be analyzed | $Mg^{2+}$ | $Ca^{2+}$ | TP |
| CPK | 2.00 | 2.00 | 1.50 |
| TG | 1.67 | 1.67 | 1.25 |
| Amy | 1.67 | 1.67 | 1.25 |
| HDL-C | 2.00 | 2.00 | 1.50 |
| ALP | 1.82 | 1.82 | 1.36 |

In FIGS. 1 to 29, each of graphs (A), (B), and (C) shows the relationship between a concentration of a component to be analyzed in the control (indicated in the x-axis) and a concentration of the component to be analyzed after a correction (indicated in the y-axis) in the example. The graphs (A), (B), and (C) show results of the corrections using $Mg^{2+}$, $Ca^{2+}$, and TP, respectively. Each of graphs (D) shows the relationship between a concentration of a component to be analyzed in the control (indicated in the x-axis) and a concentration of the component to be analyzed subjected to no correction using the standard components (indicated in the y-axis) in the comparative example. The formulae in the figures indicate the relationships and $R^2$ denotes a correlation coefficient. FIGS. 1 to 4 show results of GOT analysis, FIGS. 5 to 8 results of GPT analysis, FIGS. 9 to 12 results of γ-GTP analysis, FIGS. 13 to 16 results of CPK analysis, FIGS. 17 to 20 results of TG analysis, FIGS. 21 to 24 results of Amy analysis, FIGS. 25 to 27 results of HDL-C analysis, and FIGS. 28 and 29 results of ALP analysis. The slopes of the correlation equations obtained from these graphs are shown in Table 2 above.

As shown in Table 1 and in the respective figures, the correlation coefficients in the example were higher than those in the comparative example, and there was a high correlation between the concentrations of the components to be analyzed in the example and those in the control. Thus, according to the quantitative analysis of the present invention, the dilution ratio of a specimen in a test sample can be determined through the measurement of amounts of standard components, and thereby the concentrations of the components to be analyzed in the specimen can be measured further correctly. The multiplication by the coefficients is carried out to suppose the recovery is 100%. Hence, the multiplication does not improve the correlation coefficient indicating the measurement accuracy, but the slopes of the correlation equations come closer to "1" in both the example and comparative example, as shown in Table 2 and in the respective figures.

As described above, the quantitative analysis of the present invention allows an amount of a specimen in a test sample to be determined and thus improves the quantitativity with respect to components to be analyzed in the specimen. Such a quantitative analysis of the present invention is useful for diagnosis in clinical medical practice or the like.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A quantitative analysis for measuring a concentration of a component to be analyzed in a specimen, comprising:
    measuring an amount of a component to be analyzed in a specimen;
    measuring an amount of a standard component present homeostatically in the specimen other than the component to be analyzed;
    determining an amount of the specimen from the amount of the standard component thus measured and a known concentration of the standard component in the specimen; and
    determining a concentration of the component to be analyzed in the specimen from the amount of the specimen thus determined and the amount of the component to be analyzed thus measured.

2. The quantitative analysis according to claim 1, wherein the standard component is at least one selected from the group consisting of sodium ion, chloride ion, potassium ion, magnesium ion, calcium ion, total protein, and albumin.

3. The quantitative analysis according to claim 2, wherein the standard component is at least one selected from the group consisting of magnesium ion, calcium ion, and total protein.

4. The quantitative analysis according to claim I, wherein the specimen is an aqueous liquid specimen derived from an organism.

5. The quantitative analysis according to claim 4, wherein the aqueous liquid specimen is at least one selected from the group consisting of blood, urine, saliva, lymph, a cerebrospinal fluid, and an intercellular fluid.

6. The quantitative analysis according to claim 5, wherein the aqueous liquid specimen is blood.

7. The quantitative analysis according to claim 1, wherein the component to be analyzed is at least one selected from the group consisting of glutamic-oxaloacetic transaminase (GOT), glutamic-pyruvic transaminase (GPT), γ-glutamyl transpeptidase (γ-GTP), creatine kinase (CPK), triglyceride (TG), amylase (Amy), HDL-cholesterol (HDL-C), and alkaline phosphatase (ALP).

8. The quantitative analysis according to claim 1, wherein the specimen is retained in a porous material and is then recovered from the porous material for analysis.

9. The quantitative analysis according to claim 8, wherein the specimen is retained in the porous material, is dried, and is then recovered.

10. The quantitative analysis according to claim 8, wherein the porous material retaining the specimen is dipped in an extractant and the specimen is extracted from the porous material to be recovered.

11. The quantitative analysis according to claim 10, wherein the extractant is at least one selected from the group consisting of a buffer solution, a physiological salt solution, and purified water.

12. The quantitative analysis according to claim 10, wherein an amount of the extractant is 1 to 1000 times the porous material by volume.

13. The quantitative analysis according to claim 10, wherein a ratio of the extractant to the porous material per volume is constant.

14. The quantitative analysis according to claim 10, wherein the quantitative analysis comprises:
    measuring an amount of a component to be analyzed in a test sample containing an extractant and a specimen recovered from the porous material;
    measuring an amount of the standard component in the test sample;
    determining an amount of the specimen originally applied to the porous material from the amount of the standard component thus measured and known concentration of the standard component in the specimen; and
    determining a concentration of the component to be analyzed in the specimen originally applied to the porous material from the amount of the specimen thus determined and the amount of the component to be analyzed in the test sample thus measured.

15. The quantitative analysis according to claim 14, wherein the concentration of the component to be analyzed contained in the specimen originally applied to the porous material is determined by a formula:

$$A = Z \times (Y/X),$$

where A denotes the concentration of the component to be analyzed, Z denotes the measured amount of the component to be analyzed in the test sample, X denotes the measured amount of the standard component in the test sample, and Y denotes a known concentration value of the standard component in the specimen.

16. The quantitative analysis according to claim 1, wherein the specimen is blood serum or blood plasma, and known concentration values of the standard components contained in the specimen comprise 134 to 146 mEq/litre of sodium ion, 97 to 107 mEq/litre of chloride ion, 3.2 to 4.8 mEq/litre of potassium ion, 1.5 to 2.0 mEq/litre of magnesium ion, 8.4 to 10.2 mEq/litre of calcium ion, 6.7 to 8.3 g/100 ml of total protein, and 3.5 to 5.2 g/100 ml of albumin.

17. The quantitative analysis according to claim 1, wherein the specimen is blood serum, the standard component is magnesium ion, and the magnesium ion in the blood serum has a known concentration of 1.8 mEq/litre.

18. The quantitative analysis according to claim 1, wherein the specimen is blood serum, the standard component is calcium ion, and the calcium ion in the blood serum has a known concentration of 9.3 mEq/litre.

19. The quantitative analysis according to claim 1, wherein the specimen is blood serum, the standard component is total protein, and the total protein in the blood serum has a known concentration of 7.5 g/100 ml.

* * * * *